US006177253B1

(12) United States Patent
Erlanger et al.

(10) Patent No.: US 6,177,253 B1
(45) Date of Patent: Jan. 23, 2001

(54) SCREENING METHODS FOR THE IDENTIFICATION OF ANTI-HIV COMPOUNDS EMPLOYING A CYCLOSPORINE-SPECIFIC MONOCLONAL ANTIBODY THAT CROSS-REACTS WITH HIV-1 P24

(75) Inventors: Bernard F. Erlanger, Whitestone; Bi-Xing Chen, New York, both of NY (US)

(73) Assignee: The Trustees of Columbia University in the City of New York, New York, NY (US)

(*) Notice: Under 35 U.S.C. 154(b), the term of this patent shall be extended for 0 days.

(21) Appl. No.: 08/894,295

(22) PCT Filed: Feb. 16, 1996

(86) PCT No.: PCT/US96/02129

§ 371 Date: Jan. 8, 1998

§ 102(e) Date: Jan. 8, 1998

(87) PCT Pub. No.: WO96/25175

PCT Pub. Date: Aug. 22, 1996

Related U.S. Application Data

(63) Continuation of application No. 08/390,133, filed on Feb. 17, 1995, now Pat. No. 5,604,092.

(51) Int. Cl.[7] .................................................. G01N 33/53
(52) U.S. Cl. ..................... 435/7.1; 435/7.92; 435/7.93; 422/61; 530/388.9; 424/188.1
(58) Field of Search ..................... 435/5, 7.1; 530/388.1, 530/388.3; 436/536

(56) References Cited

U.S. PATENT DOCUMENTS

| | | | |
|---|---|---|---|
| 4,681,754 | 7/1987 | Siegl | 514/11 |
| 4,722,999 | 2/1988 | Hanschumacher et al. | 530/412 |
| 4,843,011 | 6/1989 | Sarngadharan et al. | 530/388.35 |
| 4,914,188 | 4/1990 | Dumont et al. | 530/317 |
| 5,405,785 | 4/1995 | Erlanger et al. | 436/531 |
| 5,604,092 | 2/1997 | Erlanger et al. | 435/5 |

OTHER PUBLICATIONS

Oberg et al., 1990, "Screening for New Agents", Eur. J. Clin. Microbiol. Infect. Dis. 9(7):466–471.*
Yarchoan et al., 1992, "Correlations Between The In Vitro and In Vivo Activity of Anti–HIV Agents: Implications For Future Drug Development", J. Enzym. Inhib. 6:99–111.*
Cacalano, N.A. et al. (1992) "Novel Monoclonal Antibodies to Cyclosporine A: Characterization and Epitope Mapping with Cyclosporine Analogs and Cyclophilin" Molecular Immunology, 29:107–118.
Chemical and Engineering News, Nov. 28, 1994, p. 32.
Franke, E. K. et al. (1994) "Specific Incorporation of Cyclophilin into HIV–1 Virions," Nature, 372:359–362.

Geysen et al. (1988) "Cognitive Features of Continuous Antigenic Determinants," J. Molec. Recog. 1:33–41.

Goodenow et al. (1989) "HIV–1 Isolates Are Rapidly Evolving Quasispecies: Evidence for Viral Mixtures and Preferred Nucleotide Substitutions," J. Acquired Immune Defic. Syndr. 2:344–352.

Graham et al. (1995) "Candidate AIDS Vaccines," The New England Journal of Medicine, 333(20):1331–1339. (Exhibit 3).

Holland et al. (1992) "RNA Virus Populations as Quasispecies," Curr. Topics Micro. Immunol. 176:1–20.

Luban, J. et al. (1993) "Human Immunodeficiency Virus Type 1 GAG Protein Binds to Cyclophilins A and B," Cell, 73:1067–1076.

Pantaleo, et al. (1993) "The Immunopathogenesis of Human Immunodeficiency Virus Infection," The New England Journal of Medicine, 328(5):327–335. (Exhibit 4).

Quesniaux et al. (1987) "Potential of Monoclonal Antibodies to Improve Therapuetic Monitoring of Cyclosporine," Clin. Chem., 33(1):32–37.

Quesniaux et al. (1987) "Time Specification & Cross–Reactivity of Monoclonal Antibodies," Molecular Immunology, 24(11):1159–1168.

Quesniaux et al. (1986) "Monoclonal Antibodies to Ciclosporin," Prog. Allergy, 38:108–122. (Exhibit 5).

Schran et al. (1987) "Determination of Cyclosporine Concentrations with Monoclonal Antibodies," Clin. Chem. 33(12):2225–2229.

Seaver, S. (1994) "Monoclonal Antibodies in Industry: More Difficult than Originally Thought," Genetic Engineering News, pp. 10 and 21. (Exhibit 6).

Thall, M. et al. (1994) "Functional Association of Cyclophilin a with HIV–1 Virions," Nature, 372:363–365.

* cited by examiner

Primary Examiner—Laurie Scheiner
Assistant Examiner—Jeffrey S. Parkin
(74) Attorney, Agent, or Firm—John P. White; Cooper & Dunham LLP

(57) ABSTRACT

The subject invention provides new uses for novel derivatives of cyclosporine A and antibodies directed thereto. Specifically, the derivatives and antibodies are useful in methods of treating AIDS, methods of purifying the Gag protein of HIV, methods of screening for anti-HIV compounds, and methods for detecting HIV in a subject. The derivatives and antibodies can also be incorporated into a kit useful for screening for anti-HIV compounds.

6 Claims, 14 Drawing Sheets

RH = CsA (H = Hydrogen of CsA side chain)

SCREENING METHODS FOR THE IDENTIFICATION OF ANTI-HIV COMPOUNDS EMPLOYING A CYCLOSPORINE-SPECIFIC MONOCLONAL ANTIBODY THAT CROSS-REACTS WITH HIV-1 P24

This application is a continuation of U.S. Ser. No. 08/390,133, filed Feb. 17, 1995, now U.S. Pat. No. 5,604, 092. +gi This invention was made with government support under Grant Numbers RO1 NS-15581, RO1 H1-36581 and PO1 HL-36581 and training grants 2-T32-AI-07161-11 and T32-CA-09503 from the National Institute of Health, U.S. Department of Health and Human Resources. Accordingly, the U.S. Government has certain rights in the invention.

BACKGROUND OF THE INVENTION

Throughout this application, various publications are referenced by arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed in this application.

Cyclosporine A (CsA) is a cyclic undecapeptide of fun-gal origin which is a immunosuppressive agent useful in preventing organ rejection in transplant patients (1–3).

Because the therapeutic index of CsA is narrow, it is important to measure serum cyclosporine levels in patients treated with CsA (4). This can be accomplished by high performance liquid chromatography or by RIA, with the latter procedure being the more convenient one.

It has reported, and we have confirmed (unpublished), that CSA, itself, is non-immunogenic (5). To obtain antibodies, therefore, it is necessary to link CsA to a protein carrier. The side chains of CsA, however, consist only of aliphatic groups with none of the functional groups customarily used to link a hapten to a carrier. Previous workers have made immunogenic cyclosporine C (CsC)-protein conjugates because the CsC has a threonine residue in position 2 (5). Linkage to a protein was via a hemisuccinate, using a water soluble carbodiimide as a coupling agent. Polyclonal antisera were successfully raised in this way and are routinely used to measure CsA in patients sera (5). More recently, monoclonal antibodies were prepared using an activated ester of a lysyl-CsA derivative (6).

We have chosen to use CsA, itself, as a hapten by converting it to a reactive carboxyl-containing peptide via a photochemical reaction. Coupling of this derivative to proteins has led to the successful raising of CsA-specific rabbit antibodies that can be used to measure CsA levels in sera of transplant patients under treatment with CsA.

Recently, Luban et al. (30) have shown that HIV-1 Gag protein binds to Cyclophilin A and B and that the Gag portion of SIV binds only to Cyclophilin B. We therefore determined that since Gag and CsA bind to cyclophillin, an antibody directed against CsA might bind to Gag and thereby treat HIV infection by inhibition of HIV replication. Further it is believed that the compositions of matter made according to this specification would be useful to treat AIDS.

SUMMARY OF THE INVENTION

The present invention provides a molecule having the structure:

where each R may independently be H or X, provided that at least one R is X, where X is a ligand which is produced as the result of a photochemical reaction between a precursor of X containing a photochemically activatable group and a hydrogen of cyclosporine A and which comprises a reactive group.

The invention further provides that the reactive group may be a group which is reactive with a macromolecule. In a preferred embodiment of this invention, the macromolecule may be a polypeptide. In a very preferred embodiment, the invention further provides that the. polypeptide may be a protein. In a preferred embodiment, the reactive group may be a carboxyl.

Specific examples of X may include but are not limited to the following:

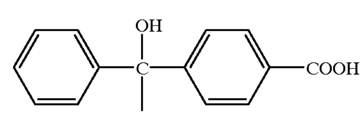

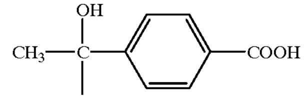

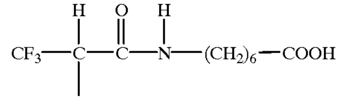

and

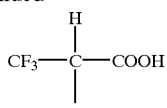

In a preferred embodiment of the invention, the probability is greater that 0.75 that only one R in the aforementioned molecule is X. In a very preferred embodiment, the probability is about 1.0.

The present invention further provides a molecule which comprises a congener of cyclosporine A characterized by the structural backbone of cyclosporine A in which one or more hydrogen atoms are replaced by one or more ligands, each such ligand both comprising a reactive group and being attached to the structural backbone of cyclosporine A at a location which a hydrogen atom has been replaced as the result of a photochemical reaction between a precursor of the ligand containing a photochemically activatable group and the hydrogen atom being replaced.

The present invention further provides an immunosuppressive agent useful for preventing organ rejection in a transplant subject comprising an amount of the aforementioned molecules effective to inhibit organ rejection in a transplant subject and a pharmaceutically acceptable carrier.

The present invention also provides a composition of matter which comprises a conjugate of a compound and the aforementioned molecule wherein the compound is bound to the molecule through the reactive group of the ligand X.

The invention further provides a composition of matter which comprises a conjugate of a macromolecule and the aforementioned molecule wherein the macromolecule is bound to the molecule through the reactive group of the ligand X.

Similarly, the invention provides a composition of matter which comprises a conjugate of a polypeptide and the aforementioned molecule wherein the polypeptide is bound to the molecule through the reactive group of the ligand X.

Moreover, the invention provides a composition of matter which comprises a conjugate of a protein and the aforementioned molecule wherein the protein is bound to the molecule through the reactive group of the ligand X.

The invention also provides a method for preventing rejection in a transplant subject comprising administering to the subject an amount of the aforementioned molecule effective to inhibit organ rejection in the transplant subject.

The subject invention further provides an antibody directed to the aforementioned composition of matter specific for cyclosporine A or congener of cyclosporine A. In accordance with the teachings of the invention the antibody may further be characterized as polyclonal or monoclonal. In addition, these antibodies may be detectably labeled.

The invention further provides a method of detecting the presence of cyclosporine A or congener of cyclosporine A in a biological tissue sample which comprises treating the biological tissue sample with the aforementioned detectably labeled antibody under conditions permitting the antibody to bind to cyclosporine A or congener and form a complex therewith, removing labeled antibody which is not bound to cyclosporine A or congener, detecting the presence of labeled antibody bound to cyclosporine A or congener and thereby detecting the presence of cyclosporine A or congener in the biological tissue sample.

The invention further provides another method of detecting the presence of cyclosporine A or a congener of cyclosporine A in a biological tissue sample which comprises treating the biological tissue sample with the aforementioned unlabeled antibody under conditions permitting the antibody to bind to cyclosporine A or congener and form a complex therewith, removing antibody which is not bound to cyclosporine A or congener, treating the complex with a labeled antibody directed to the unlabeled antibody under conditions such that the labeled antibody binds to the unlabeled antibody of the complex, removing labeled antibody which is not bound to the complex, detecting the presence of labeled antibody bound to the complex and thereby detecting the presence of cyclosporine A or congener in the biological tissue sample.

Additionally, this invention provides a method of determining the concentration of cyclosporine A or congener of cyclosporine A in a biological fluid sample which comprises, contacting a solid support with an excess of the aforementioned composition of matter under conditions permitting the composition of matter to attach to the surface of the solid support, contracting a predetermined volume of biological fluid sample with a predetermined amount of the aforementioned labeled antibody under conditions such that the cyclosporine A or congener in the sample binds to the labeled antibody and forms a complex therewith, contacting the resulting complex to the solid support to the surface of which the composition of matter is attached under conditions permitting the labeled antibody of the complex to bind to the composition of matter, treating the solid support so that only the composition of matter and labeled antibody of the complex bound thereto remain, quantitatively determining the amount of labeled antibody of the complex bound to the composition of matter, and thereby determining the concentration of cyclosporine A or congener in the biological fluid sample.

This invention provides another method of determining the concentration of cyclosporine A or congener of cyclosporine A in a biological fluid sample which comprises contacting a solid support with an excess of the aforementioned composition of matter under conditions permitting the composition of matter to attach to the solid support, contacting a predetermined volume of biological fluid sample with a predetermined amount of the aforementioned antibody under conditions such that the cyclosporine A or congener in the sample binds to the antibody and forms a complex therewith, contacting this complex with a predetermined amount of labeled antibody directed to the unlabeled antibody under conditions such that the labeled antibody binds to the unlabeled antibody complex of the prior step and forms a labeled complex therewith, contacting the resulting labeled complex to the solid support to the surface of which the composition of matter is attached under conditions permitting the unlabeled antibody bound to the labeled antibody of the labeled complex to bind to the composition of matter, treating the solid support so that only the composition of matter and labeled complex bound thereto remain, quantitatively determining the amount of labeled antibody of the labeled complex bound to the unlabeled antibody which is in turn bound to the composition of matter, and thereby determining the concentration of cyclosporine A or congener in the biological fluid sample.

The invention also provides a method of determining the concentration of cyclosporine A or congener of cyclosporine A in a biological fluid sample by radioimmunoassay which comprises radioactively labeling a predetermined amount of a substance comprising cyclosporine A, congener of cyclosporine A or the aforementioned composition of matter, adding the predetermined amount of radiolabeled substance to the biological fluid sample, contacting this mixture with a predetermined amount of the aforementioned unlabeled antibody under conditions suitable to permit the antibody to bind to the cyclosporine A or congener in the biological fluid sample and the labeled substance, removing any unbound radiolabeled substance, quantitatively determining the amount of labeled substance bound to the antibody, and thereby determining the concentration of cyclosporine A or congener in the biological fluid sample.

The invention also provides a method of monitoring levels of cyclosporine A or congener of cyclosporine A in a subject which comprises taking biological fluid samples from a subject at predetermined intervals and determining the amount of cyclosporine A or congener in each biological fluid sample according to the aforementioned assays.

The invention additionally provides a method for producing a monoclonal auto-anti-idiotypic antibody which comprises contacting lymphoid calls of an animal under suitable conditions with an effective antibody-raising amount of the aforementioned composition of matter, collecting the lymphoid cells at a suitable time after the contacting, fusing the collected lymphoid cells with appropriate myelona cells to produce a series of hybridoma cells each of which produces a monoclonal antibody, screening under suitable conditions the series of hybridoma cells so produced to identify those which secrete a monoclonal antibody capable of binding to an antibody directed to the aforementioned composition of matter, separately culturing a hybridoma cell so identified in an appropriate medium, and separately recovering under suitable conditions the monoclonal anti-idiotypic antibody produced by the hybridona cell.

The invention further provides an antibody directed to the aforementioned monoclonal auto-anti-idiotypic antibody. Additionally, the invention provides an antibody directed to the aforementioned antibodies. These antibodies directed to other antibodies may be used in an immunoregulatory substance useful for preventing organ rejection in a transplant subject in an amount effective to inhibit organ rejection in a transplant subject and a pharmaceutically acceptable carrier.

The invention further provides a method of reducing the amount of cyclosporine A or congener in a subject which comprises administering intravenously to the subject an amount of the aforementioned antibody effective to reduce the amount of cyclosporine A and permitting the antibody to bind to the excess cyclosporine A, thereby rendering the excess cyclosporine A ineffective.

The invention also provides a method of reducing the amount of endogenous immunoregulatory substances, or other biologically active substances which are endogenous, which share epitopes with cyclosporine A or congener of cyclosporine A in a subject which comprises administering intravenously to the subject an amount of aforementioned antibody or fragment thereof effective to reduce the amount of endogenous substances and permitting the antibody or fragment thereof to bind to the excess endogenous substances, thereby rendering the excess endogenous substances ineffective.

The invention further provides a method of testing the potential of a pharmacological agent as an immunoactive agent which comprises running an immunochemical assay competitive between the pharmacological agent and known amounts of labeled cyclosporine A or congener of cyclosporine A with the aforementioned antibody under conditions such that the antibody forms complexes with the pharmacological agent and cyclosporine A or congener and determining the displacement from the antibody of labeled cyclosporine A or congener by the pharmacological agent.

In addition, the present invention provides a composition of matter which comprises aminodextran and the aforementioned molecule, wherein the aminodextran is bound to the molecule through the reactive group of ligand X.

The invention also provides a method of testing a pharmalogical agent for immunosuppressive activity which comprises contacting cells with the composition of matter above under conditions such that the composition of matter causes agglutination of cells, contacting the resulting agglutinated cells with the pharmalogical agent, an inhibition of agglutination being indicative that the pharmalogical agent has immunosuppressive activity.

The subject invention also provides a method of treating AIDS in a subject which comprises administration of an antibody which specifically binds to N-methyl leucine residues 9 and 10 of cyclosporine to a subject in an amount effective to inhibit HIV replication and thereby treat AIDS.

The subject invention further provides a method of treating AIDS in a subject which comprises administration of a composition of matter, wherein the composition of matter comprises a compound having the structure:

wherein a plurality of R's are X and the remainder are H, wherein X is a ligand comprising a reactive group and wherein X is bonded to the compound by a photochemical reaction between a hydrogen of cyclosporine A and a photochemically activatable precursor of X;

and a polypeptide coupled to the compound through the reactive group on X;

in an amount effective to produce an antibody which specifically binds to N-methyl leucine residues 9 and 10 of cyclosporine to inhibit HIV replication and thereby treat AIDS.

The subject invention also provides a method of purifying the Gag protein of HIV which comprises:

a) contacting a sample known to contain the Gag protein with an antibody which specifically binds to N-methyl leucine residues 9 and 10 of cyclosporine under conditions such that the antibody binds to and forms a complex with the Gag protein;

b) isolating the antibody-protein complex formed in (a); and c) separating the protein from the isolated antibody-protein complex from (b).

The subject invention also provides a method of screening for anti-HIV compounds which comprises:

a) immobilizing a composition of matter having the structure:

wherein a plurality of R's are X and the remainder are H, wherein X is a ligand comprising a reactive group and wherein X is bonded to the Compound by a photochemical reaction between a hydrogen of cyclosporine A and a photochemically activatable precursor of X;

b) contacting the immobilized composition of matter from (a) with a mixture of the compound suspected of having anti-HIV activity and a detectably labeled antibody which specifically binds to N-methyl leucine residues 9 and 10 of cyclosporine under conditions ailowing for the labeled antibody to bind to the immobilized composition of matter from (a) and form a complex therewith;

c) separating any unbound labeled antibody from the complex formed in (b);

d) detecting any labeled antibody bound to the complex in (c); and e) quantitating the amount of labeled antibody from (d).

The subject invention further provides a kit for of screening for anti-HIV compounds which comprises:

a) a plate comprising a plurality of wells;

b) a composition of matter immobilized upon the wells, wherein the composition of matter has the structure:

wherein a plurality of R's are X and the remainder are H, wherein X is a ligand comprising a reactive group and wherein X is bonded to the compound by a photochemical reaction between a hydrogen of cyclosporine A and a photochemically activatable precursor of X; and c) a solution comprising a detectably labeled antibody which specifically binds to N-methyl leucine residues 9 and 10 of cyclosporine.

The subject invention also provides a method for detecting HIV in a subject which comprises:

a) obtaining a serum sample from a subject;

b) contacting the serum sample with a detectably labeled antibody which specifically binds to N-methyl loucine residues 9 and 10 of cyclosporine under conditions permitting the detectably labeled antibody to bind to and form a complex with a Gag protein on any HIV in the serum sample;

c) removing any antibodies which are not part of the complex of (b); and d) detecting the presence of antibodies in the serum sample, thereby detecting the presence of HIV in the subject.

BRIEF DESCRIPTION OF THE FIGURES

FIG. 5A is a structural diagram of cyclosporine A (CsA). FIG. 5B is a three-dimensional space-filling model of CsA based on X-ray crystallography and NMR data.

DETAILED DESCRIPTION OF THE INVENTION

The present invention provides a molecule having the structure:

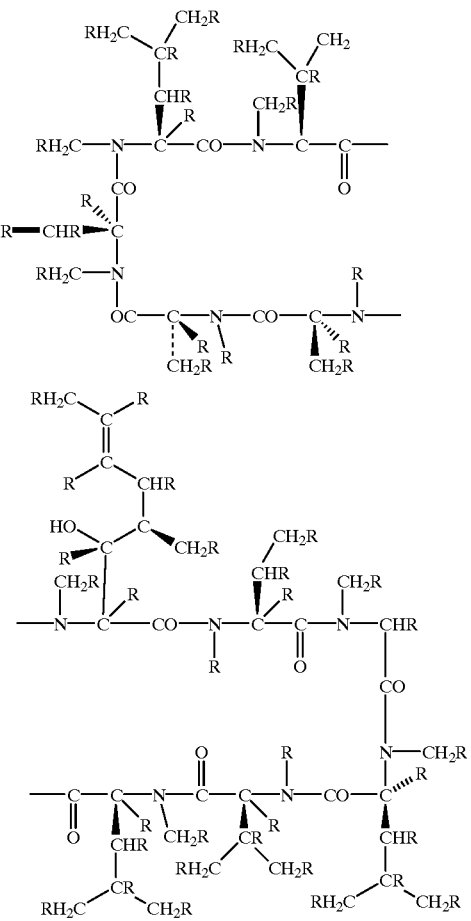

wherein each R may independently be H or X, provided that at least one R is X, where X is a ligand which is produced as the result of a photochemical reaction between a precursor of X containing a photochemically activatable group and a hydrogen of cyclosporine A and which comprises a reactive group.

The invention further provides that the reactive group may be a group which is reactive with a macromolecule. Examples of such macromolecules include, but are not limited to, polysaccharides, complex carbohydrates, and any organic polymers including but not limited to polyacrylamide, polynitrocellulose, and polystyrene. In a preferred embodiment of this invention, the macro-molecule may be a polypeptide. In a very preferred embodiment, the invention further provides that the polypeptide may be a protein.

In a further embodiment of the invention, the reactive group may be an ester, carbonyl, amine or phosphonamide. In a preferred embodiment, the reactive group may be a carboxyl.

Photochemical reactions are well-known in the art (7) and it is to be understood that X may be any ligand which is produced as the result of a photochemical reaction between a precursor of X containing a photo-chemically activatable group and a hydrogen of cyclosporine A and which comprises a reactive group.

Specific examples of X may include but are not limited to the following:

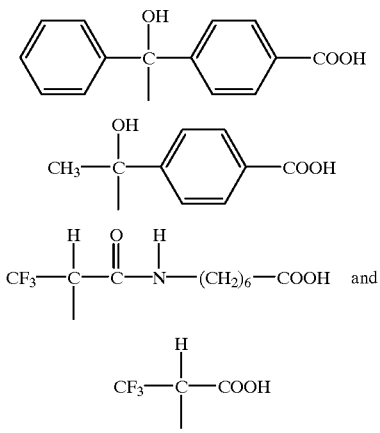

In a preferred embodiment of the invention, the probability is greater than 0.75 that only one R in the aforementioned molecule is X. In a very preferred embodiment, the probability is about 1.0.

The present invention further provides a molecule which comprises a congener of cyclosporine A in which one or more hydrogen atoms are replaced by one or more ligands, each such ligand both comprising a reactive group and being attached to the structural backbone of cyclosporine A at a location which a hydrogen atom has been replaced as the result of a photochemical reaction between a precursor of the ligand containing a photochemically activatable group and the hydrogen atom being replaced.

Congeners of cyclosporine A currently exist in the literature (5, 8) and it is anticipated that many more may be developed. It is foreseen that the novelties of the subject application which are applicable to cyclosporine A may also be applicable to such congeners.

Figure 5A:
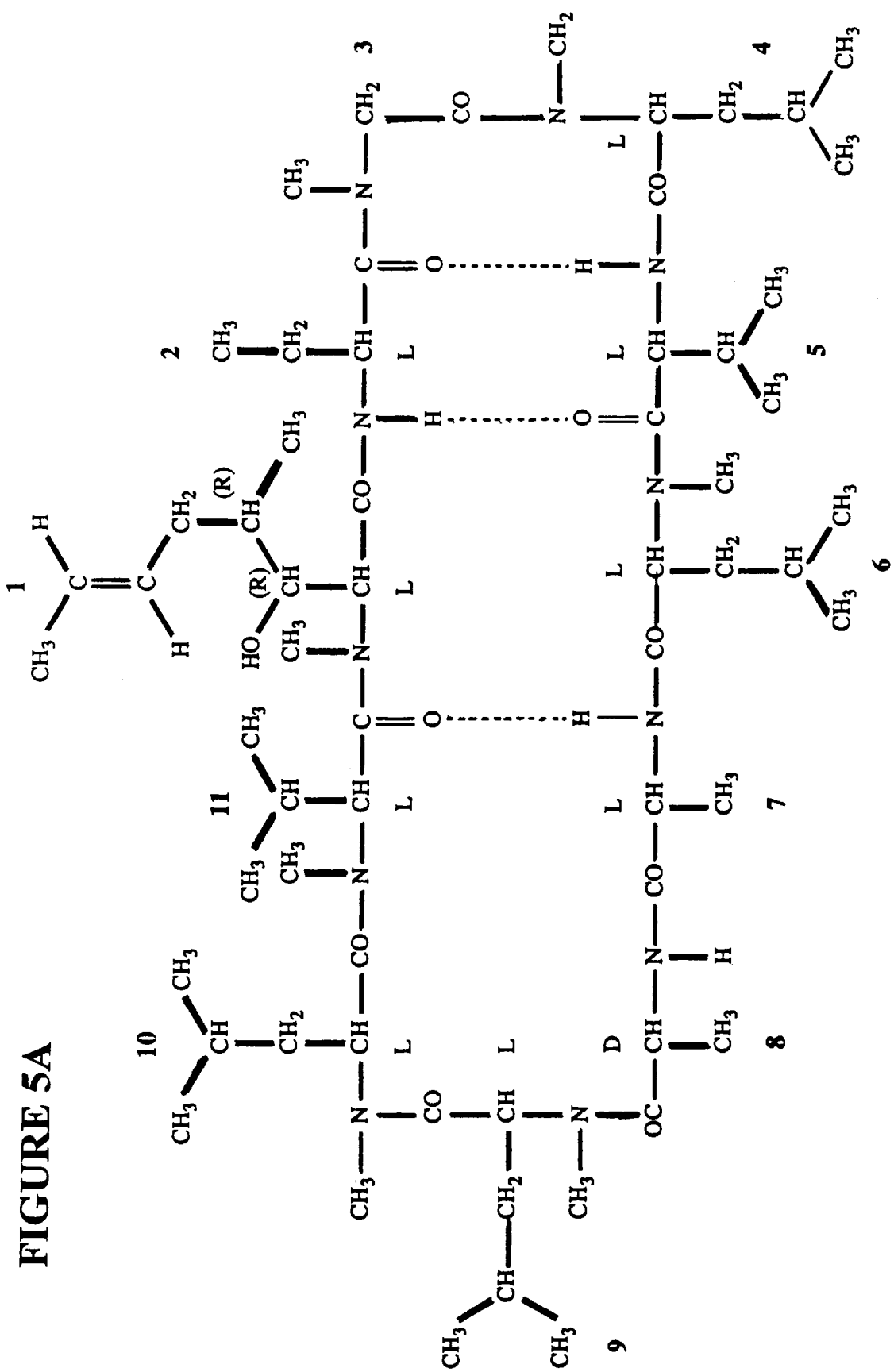
FIGS. 5A and 5B.

The basic structure of cyclosporine A is represented in FIG. 5A. Examples of such congeners include, but are not limited to, cyclosporine A with:

(a) alanine at position 2;
(b) threonine at position 2;
(c) valine at position 2;
(d) norvaline at position 2 and 5; and
(e) alpha-amino butyric acid at position 7.

The present invention further provides an immunosuppressive agent useful for preventing organ rejection in a transplant subject comprising an amount of the aforementioned molecules effective to inhibit organ rejection in a transplant subject and a pharmaceutically acceptable carrier.

As used herein, the term "pharmaceutically acceptable carrier" encompasses any of the standard pharmaceutical carriers. Such carriers are well-known in the art and may include, but are not intended to be limited to, any of the standard pharmaceutical carriers such as phosphate buffered saline solution, water, emulsions such as oil/water emulsion, and various types of wetting agents.

The aforementioned immunosuppressive compositions may be superior to cyclosporine A in several ways. First, the compositions may avoid the toxicity problems inherent with cyclosporine A, specifically kidney damage. Second, these compositions may be soluble and thereby preferable for dosage regulation.

The present invention also provides a composition of matter which comprises a conjugate of a compound and the aforementioned molecule wherein the compound is bound to the molecule through the reactive group of the ligand X. The general process for preparation of antigenic hapten-carrier conjugates is known in the art (9).

The invention further provides a composition of matter which comprises a conjugate of a macromolecule and the aforementioned molecule wherein the macromolecule is bound to the molecule through the reactive group of the ligand X.

Similarly, the invention provides a composition of matter which comprises a conjugate of a polypeptide and the aforementioned molecule wherein the polypeptide is bound to the molecule through the reactive group of the ligand X.

Moreover, the invention provides a composition of matter which comprises a conjugate of a protein and the aforementioned molecule wherein the protein is bound to the molecule through the reactive-group of the ligand X. Again, it is to be understood that the scope of the invention includes any protein capable of being bound to the molecule. Specific examples of this protein includes bovine serum albumin, rabbit serum albumin, keyhole limpet hemocyanin, ovalbumin, or any globulin including but not limited to thyroglobulin.

The invention also provides a method for preventing rejection in a transplant subject comprising administering to the subject an amount of the aforementioned molecule effective to inhibit organ rejection in the transplant subject.

The subject invention further provides an antibody directed to the aforementioned composition of matter specific for cyclosporine A or congener of cyclosporine A. In accordance with the teachings of the invention, the antibody, as cited herein and in the following uses thereof, may further be characterized as polyclonal or monoclonal.

In addition, these antibodies may be detectably labeled. Such labels are well-known in the art and include but are not limited to enzyme labels, fluorescent labels, and radioactive labels such as fluorophore or biotinylated labels.

The invention further provides a method of detecting the presence of cyclosporine A or congener of cyclosporine A in a biological tissue sample which comprises treating the biological tissue sample with the aforementioned detectably labeled antibody under conditions permitting the antibody to bind to cyclosporine A or congener and form a complex therewith, removing labeled antibody which is not bound to cyclosporine A or congener, detecting the presence of labeled antibody bound to cyclosporine A or congener and thereby detecting the presence of cyclosporine A or congener in the biological tissue sample.

Detecting the presence of cyclosporine A or congener in biological tissue sample is useful since the toxic effects of cyclosporine A include damage to tissues, particularly kidney. Accordingly, in a preferred embodiment of the method of detecting the presence of cyclosporine A or congener, the biological tissue sample is kidney. However, the biological tissue sample is not intended to be limited to kidney and includes other biological tissues such as liver.

Additionally, this invention provides a method of determining the concentration of cyclosporine A or congener of cyclosporine A in a biological fluid sample which comprises, contacting a solid support with an excess of the aforementioned composition of matter under conditions permitting the composition of matter to attach to the surface of the solid support, contacting a predetermined volume of biological fluid sample with a predetermined amount of aforementioned labeled antibody under conditions such that the cyclosporine A or congener in the sample binds to the labeled antibody and forms a complex therewith, contacting the resulting complex to the solid support to the surface of which the composition of matter is attached under conditions permitting the labeled antibody of the complex to bind to the composition of matter, treating the solid support so that only the composition of matter and labeled antibody of the complex bound thereto remain, quantitatively determining the amount of labeled antibody of the complex bound to the composition of matter, and thereby determining the concentration of cyclosporine A or congener in the biological fluid sample.

The aforementioned biological fluid and the biological fluid used in the following methods for determining the concentration of cyclosporine A or congener thereof and method for monitoring levels of cyclosporine A or congener thereof, may be, but is not limited to blood, urine, feces or extracts of tissue.

This invention provides another method of determining the concentration of cyclosporine A or congener of cyclosporine A in a biological fluid sample which comprises contacting a solid support with an excess of the aforementioned composition of matter under conditions permitting the composition of matter to attach to the surface of the solid support, contacting a predetermined volume of biological fluid sample with a predetermined amount of the aforementioned antibody under conditions such that the cyclosporine A or congener in the sample binds to the antibody and forms a complex therewith, contacting this complex with a predetermined amount of labeled antibody directed to the unlabeled antibody under conditions such that the labeled antibody binds to the unlabeled antibody complex of the prior step and forms a labeled complex therewith, contacting the resulting labeled complex to the solid support to the surface of which the composition of matter is attached under conditions permitting the unlabeled antibody bound to the labeled antibody of the labeled complex to bind to the composition of matter, treating the solid support so that only the composition of matter and labeled complex bound thereto remain, quantitatively determining the amount of labeled antibody of the labeled complex bound to the unlabeled antibody which is in turn bound to the composition of matter, and thereby determining the concentration of cyclosporine A or congener in the biological fluid sample.

In the two aforementioned methods of determining the concentration of cyclosporine A or congener, the composition of matter may be attached to the surface of the solid support by covalent or noncovalent bonds.

The invention also provides a method of determining the concentration of cyclosporine A or congener of cyclosporine A in a biological fluid sample by radioimmunoassay which comprises radioactively labeling a predetermining amount of a substance comprising cyclosporine A, congener of cyclosporine A or the aforementioned composition of matter, adding the predetermined amount of radiolabeled substance to the biological fluid sample, contacting this mixture with a predetermined amount of the aforementioned unlabeled antibody under conditions suitable to permit the antibody to bind to the cyclosporine A or congener in the biological fluid sample and the labeled substance, removing any unbound radiolabeled substance, quantitatively determining the amount of labeled substance bound to the antibody, and thereby determining the concentration of cyclosporine A or congener in the biological fluid sample.

Methods of determining the concentration of cyclosporine A or congener in the biological fluid sample from data concerning labeled complex is well-known in the art. One such example includes comparing the data to a standard curve.

It is to be understood that it is within the scope of the present invention to use other types of assays and detectable labels with the aforementioned antibodies for determining the concentration of cyclosporine A in a biological fluid sample.

The invention also provides a method of monitoring levels of cyclosporine A or congener of cyclosporine A in a subject which comprises taking biological fluid samples from a subject at predetermined intervals and determining the amount of cyclosporine A or congener in each biological fluid sample according to the aforementioned assays.

The invention additionally provides a method for producing a monoclonal auto-anti-idiotypic antibody which comprises contacting lymphoid cells of an animal under suitable conditions with an effective antibody-raising amount of the aforementioned composition of matter, collecting the lymphoid cells at a suitable time after the contacting, fusing the collected lymphoid cells with appropriate myeloma cells to produce a series of hybridoma cells each of which produces a monoclonal antibody, screening under suitable conditions the series of hybridoma cells so produced to identify those which secrete a monoclonal antibody capable of binding to an antibody directed to the aforementioned composition of matter, separately culturing a hybridoma cell so identified in an appropriate medium, and separately recovering under suitable conditions the monoclonal anti-idiotypic antibody produced by the hybridoma cell. Methods of producing monoclonal auto-anti-idiotypic antibodies are previously known in the art as outlined in U.S. Pat. No. 5,114,010 issued Sep. 1, 1992, the contents of which are hereby incorporated by reference.

The invention further provides an antibody directed to the aforementioned monoclonal auto-anti-idiotypic antibody. Additionally, the invention provides an antibody directed to each of the aforementioned antibodies which are specific for cyclosporine A or congener thereof. These antibodies may be used- in an immunoregulatory substance useful for preventing organ rejection in a transplant subject in an amount effective to inhibit organ rejection in a transplant subject and a pharmaceutically acceptable carrier.

The invention further provides a method of reducing the amount of cyclosporine A or congener in a subject which comprises administering intravenously to the subject an amount of the aforementioned antibody effective to reduce the amount of cyclosporine A and permitting the antibody to bind to the excess cyclosporine A, thereby rendering the excess cyclosporine A ineffective.

The invention also provides a method of reducing the amount of endogenous immunoregulatory substances, or other biologically active substances which are endogenous, which share epitopes with cyclosporine A or congener of cyclosporine A in a subject which comprises administering intravenously to the subject an amount of aforementioned antibody or fragment thereof effective to reduce the amount of endogenous substances and permitting the antibody or fragment thereof to bind to the excess endogenous substances, thereby rendering the excess endogenous substances ineffective.

The invention also provides a method of testing a pharmalogical agent for immunosuppressive activity which comprises contacting cells with the composition of matter above under conditions such that the composition of matter causes agglutination of cells, contacting the resulting agglutinated cells with the pharmalogical agent, an inhibition of agglutination being indicative that the pharmalogical agent has immunosuppressive activity. Preferably, the cells above are either T or B-cells.

The subject invention also provides a method of treating AIDS in a subject which comprises administration of an antibody which specifically binds to N-methyl leucine residues 9 and 10 of cyclosporine to a subject in an amount effective to inhibit HIV replication and thereby treat AIDS.

In a preferred embodiment of the above described invention the antibody which specifically binds to N-methyl leucine residues 9 and 10 of cyclosporine is the monoclonal antibody B-11 1.4 produced by the hybridoma cell line having ATCC Accession No. HP-11853 HP-11853. This hybridoma was deposited on Feb. 17, 1995 in accordance with the Budapest Treaty with the American Type Culture Collection, 12301 Parklawn Drive, Rockville, Md., 20852 U.S.A.

The monoclonal antibodies of the subject invention include whole monoclonal antibodies as well as antigen binding fragments thereof. Examples of such fragments are well known to those of ordinary skill in the art and are referred to as Fab, Fab' or F(ab')2 antibody fragments. In a preferred embodiment the monoclonal antibody fragment is a Fab' fragment. In another-preferred embodiment the monoclonal antibody fragment is a F(ab')$_2$ fragment. Methods of producing the antibody fragments are also known to those of ordinary skill in the art. By way of example, the Fab' fragment of the above-disclosed monoclonal antibody can be produced by papain digestion of the monoclonal antibody. Similarly, the F(ab')$_2$ fragment can be produced by pepsin digestion of the monoclonal antibody.

In one embodiment of this invention the monoclonal antibody is a murine antibody. In another embodiment the monoclonal antibody is a chimeric monoclonal antibody. In still another embodiment the monoclonal antibody is a humanized monoclonal antibody. However, in the preferred embodiment the monoclonal antibody is a human monoclonal antibody.

For the purposes of this invention, a "chimeric" monoclonal antibody is a murine monoclonal antibody comprising constant region fragments ($F_c$) from a different animal. In a preferred embodiment of this invention, the chimeric monoclonal antibody comprises human FC and murine $F_{ab}$. For the purposes of this invention, a "humanized" monoclonal antibody is a murine monoclonal antibody in which human protein sequences have been substituted for all the murine protein sequences except for the murine complement determining regions (CDR) of both the light and heavy chains.

In an additional embodiment the subject antibody, or fragment thereof, can be linked to a cytotoxic agent to form an immunotoxin. Toxins useful as cytotoxic agents coupled to antibodies are well known to those of ordinary skill in the art and include, but are not limited to, toxins from bacteria diphtheria, pseudomonas or shigella or the castor bean toxin ricin. Examples of the use of toxins coupled to antibodies or to protein fragments for expression in cells to treat HIV infection include Harrison et al., U.S. Pat. No. 5,306,631, issued Apr. 26, 1994 and Ardman, U.S. Pat. No. 5,252,556, issued Oct. 12, 1993, the contents of which are hereby incorporated in their entirety into the subject specification by reference.

The subject invention further provides a method of treating AIDS in a subject which comprises administration of a composition of matter, wherein the composition- of matter comprises a compound having the structure:

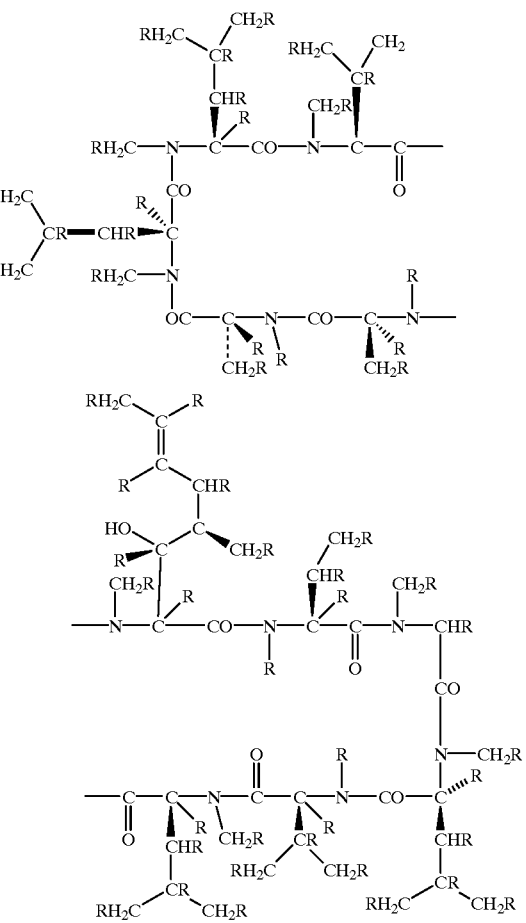

wherein a plurality of R's are X and the remainder are H, wherein X is a ligand comprising a reactive group and wherein X is bonded to the compound by a photochemical reaction between a hydrogen of cyclosporine A and a photochemically activatable precursor of X:
and a polypeptide coupled to the compound through the reactive group on X;
in an amount effective to produce an antibody which specifically binds to N-methyl leucine residues 9 and 10 of cyclosporine to inhibit HIV replication and thereby treat AIDS.

In the practice of the above-described method the polypeptide is a protein. Proteins useful in the practice of the claimed invention are known to those of ordinary skill in the art and include but are not limited to bovine serum albumin, rabbit serum albumin, and keyhole limpit heomycin.

In the practice of the methods of treatment of this invention the compositions of matter may be administered as part of a pharmaceutical composition which comprises any of the compositions of matter or antibodies and a pharmaceutically acceptable carrier. In the preferred embodiment of this invention, the compounds are administered to the subject as a pharmaceutical composition.

As used herein, the term "pharmaceutically acceptable carrier" encompasses any of the standard pharmaceutical carriers such as an organic or inorganic inert carrier material suitable for enteral or parenteral administration which include, but are not limited to, water, gelatin, gum arabic, lactose, starches, magnesium stearate, talc, vegetable oils, polyalkylene glycols, petroleum gelly, etc. The pharmacological preparations can be made up in solid form such as tablets, dragees, suppositories or capsules, or in liquid form such as solutions, suspensions, or emulsions. The preparations may be sterilized and/or contain adjuvants such as preserving, stabilizing, wetting or emulsifying agents, salts for varying the osmotic pressure, or buffers. Such preparations may also contain other therapeutic agents.

For the purposes of this invention, the term "pharmaceutically effective amount" of the compound means any amount of the compound which, when incorporated in the pharmaceutical composition, will be effective to inhibit HIV replication and thereby treat AIDS but less than an amount which would be toxic to the subject. In the practice of this invention the amount of the composition of matter incorporated in the pharmaceutical composition may vary widely. Factors considered when determining the precise amount are well known to those skilled in the art. Examples of such factors include, but are not limited to, the subject being treated, the specific pharmaceutical carrier and route of administration being employed and the frequency with which the composition is to be administered. In a preferred embodiment of this invention, the pharmaceutically effective amount of the compound is in the range of 10 picomolar to 10 millimolar. In a particularly preferred embodiment the pharmaceutically effective amount is about 10 micromolar.

In the practice of this invention, the administration of the composition may be effected by any of the well known methods including, but not limited to, oral, intravenous, intraperitoneal, intramuscular, subcutaneous or topical administration.

The subject invention also provides a method of purifying the Gag protein of HIV which comprises:

a) contacting a sample known to contain the Gag protein with an antibody which specifically binds to N-methyl leucine residues 9 and 10 of cyclosporine under conditions such that the antibody binds to and forms a complex with the Gag protein;

b) isolating the antibody-protein complex formed in (a); and c) separating the protein from the isolated antibody-protein complex from (b).

In a preferred embodiment of the above-described method step (a) further comprises immobilizing the antibody on a matrix and contacting the protein with the immobilized antibody. In the practice of this method the matrix may be any matrix known to those of ordinary skill in the art which allows for the immobilization of an antibody. Examples include agarose beads, PVC microtiter plates and nitrocellulose, either as a sheet or as fused to a microtiter plate. In a preferred embodiment the matrix comprises agarose beads.

An example of the practice of one embodiment of the invention when activated beads are used comprises (1) dialyzing the antibody against of binding buffer of 0.5 M sodium phosphate (pH 7.5); (2) preparing a solution of the antibody at the desired concentration in 0.5 M (pH 7.5) at a ratio of between 5 to 10 mg of antibody per milliliter of beads to yield a high-capacity column; (3) adding the activated beads, prepared by any method known to those of skill in the art; and (4) mixing overnight at approximately 4° C. with constant agitation.

In another preferred embodiment of the above-described method step (a) further comprises:

i) contacting the antibody with biotin under conditions such that the antibody is biotinylated;

ii) contacting the solution known to contain the Gag protein with the biotinylated antibody from step (i) to form a complex with the Gag protein; and iii) contacting the biotinylated antibody-protein complex from (ii) with a matrix comprising streptavidin and agarose under conditions such that the biotin binds to the streptavidin in the matrix.

As an example of the practice of the above-described method the biotinylated antibodies are prepared by (1) combining a biotin ester, for example comprising a solution of N-hydroxysuccinimide biotin at 10 mg/ml in dimethyl sulfoxide, with the antibody at a ratio of between 25–250 μg of ester per milligram of antibody incubating at room temperature for approximately 4 hr; (2) adding approximately 20 μl of 1M $NH_4Cl$ per 250 μg of ester and incubate for approximately 10 min at room temperature; (3) adding sufficient biotinylated antibody to the solution containing the Gag protein to bind the majority of the antigen (determined by prior titrations); (4) incubating at approximately 4° C. for approximately 1 hour; (5) at a temperature of approximately 4° C., passing the antigen-antibody solution through a volume of uncoupled agarose beads equivalent to or larger than the volume of the streptavidin-agarose beads that will be used to collect the antibody-antigen complex; and (6) at a temperature of approximately 4° C., collecting the biotinylated antibodies by passing the antigen-antibody solution through a streptavidin-agarose column at a rate of approximately 7.5 to 10 ml/hr;

An example of the condition of the separation of step (c) above includes (1) washing the column with an appropriate number of volumes of binding buffer; and.(2) eluting the antigen by sequentially passing samples of elution buffer through the column and collecting the fractions eluted.

In a preferred embodiment of any of the above-described methods the antibody which specifically binds to N-methyl leucine residues 9 and 10 of cyclosporine is the monoclonal antibody B-11 1.4 produced by the hybridoma cell line having ATCC Accession No. HB-11853.

The subject invention also provides a method of screening for anti-HIV compounds which comprises:

a) immobilizing a composition of matter having the structure:

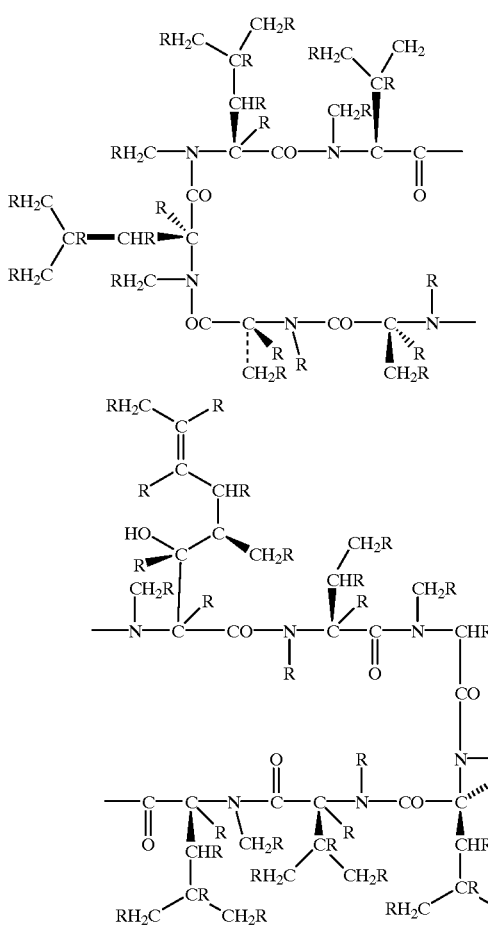

wherein a plurality of R's are X and the remainder are H, wherein X is a ligand comprising a reactive group and wherein X is bonded to the compound by a photochemical reaction between a hydrogen of cyclosporine A and a photochemically activatable precursor of X;

b) contacting the immobilized composition of matter from (a) with a mixture of the compound suspected of having anti-HIV activity and a detectably labeled antibody which specifically binds to N-methyl leucine residues 9 and 10 of cyclosporine under conditions allowing for the labeled antibody to bind to the immobilized composition of matter from (a) and form a complex therewith;

c) separating any unbound labeled antibody from the complex formed in (b);

d) detecting any labeled antibody bound to the complex in (c); and e) quantitating the amount of labeled antibody from (d).

As an example of the practice of the above-described method (1) the composition of matter is bound to the bottom of wells, preferably PVC microtiter plates, by adding approximately 50 µl of a solution of the composition of matter (approximately 20 µg/ml), all dilutions done in PBS; (2) incubating the plates at room temperature for approximately 2 hours; (3) washing the plates at least twice with PBS; (4) filling the plates with a blocking buffer, for example 3% BSA/PBS with 0.02% sodium azide incubating at room temperature for between approximately 2 hours to overnight; (5) washing the plates at least twice with PBS; (6) adding the mixture of the labeled antibody and compound suspected of having anti-HIV activity and a detectably labeled antibody, incubating at room temperature for approximately 2 hours; and (7) removing unbound antibodies and compound by multiple washes with PBS.

In a preferred embodiment of the above-described method the detectably labeled antibody which specifically binds to N-methyl leucine residues 9 and 10 of cyclosporine is the monoclonal antibody B-11 1.4 produced by the hybridoma cell line having ATCC Accession No. HB-11853.

In the practice of the above-described method the detectably labeled antibody is labeled with an enzyme, dye, fluorescent marker, colored bead, radioactive isotope or biotin.

In a preferred embodiment the compound suspected of having anti-HIV activity will be a polypeptide.

The subject invention further provides a kit for of screening for anti-HIV compounds which comprises:

a) a plate comprising a plurality of wells;

b) a composition of matter immobilized upon the wells, wherein the composition of matter has the structure:

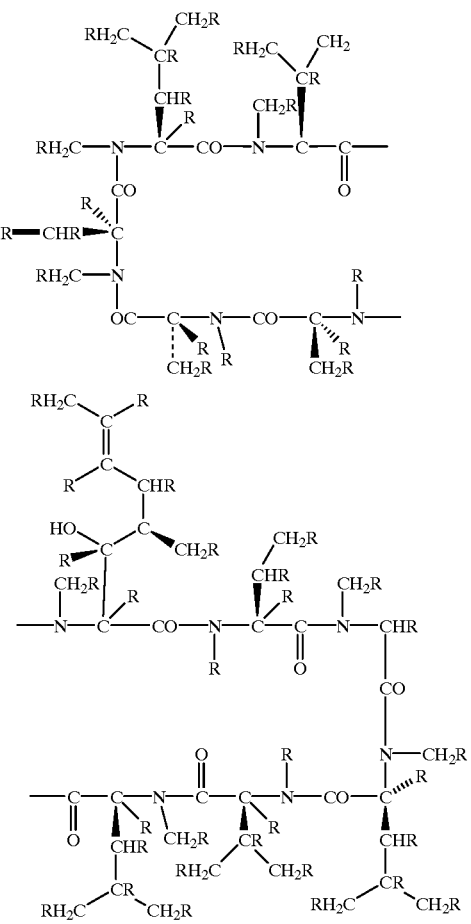

wherein a plurality of R's are X and the remainder are H, wherein X is a ligand comprising a reactive group and wherein X is bonded to the compound by a photochemical reaction between a hydrogen of cyclosporine A and a photochemically activatable precursor of X; and c) a solution comprising a detectably labeled antibody which specifically binds to N-methyl leucine residues 9 and 10 of cyclosporine.

In a preferred embodiment of the above described kit the detectably labeled antibody which specifically binds to N-methyl leucine residues 9 and 10 of cyclosporine is the monoclonal antibody B-11 1.4 produced by the hybridoma cell line having ATCC Accession No. HB-11853.

In the use of the above-described kit the detectably labeled antibody is labeled with an enzyme, dye, fluorescent marker, colored bead, radioactive isotope or biotin.

In a preferred embodiment the wells will comprise PVC plates.

The subject invention also provides a method for detecting HIV in a subject which comprises:

a) obtaining a serum sample from a subject;
b) contacting the serum sample with a detectably labeled antibody which specifically binds to N-methyl leucine residues 9 and 10 of cyclosporine under conditions permitting the detectably labeled antibody to bind to and form a complex with a Gag protein on any HIV in the serum sample;
c) removing any antibodies which are not part of the complex of (b); and
d) detecting the presence of antibodies in the serum sample, thereby detecting the presence of HIV in the subject.

In the practice of the above-described method the antibody may be immobilized such as being bound to agarose beads or nitrocellulose or PVC as described above.

In a preferred embodiment of the above-described method the detectably labeled antibody which specifically binds to N-methyl leucine residues 9 and 10 of cyclosporine is the monoclonal antibody B-11 1.4 produced by the hybridoma cell line having ATCC Accession No. HB-11853.

In the practice of the above-described method the detectably labeled antibody is labeled with an enzyme, dye, fluorescent marker, colored bead, radioactive isotope or biotin.

Practice of, and determination of the optimal conditions for, any of the methods of the subject invention is within the skill of the ordinary artisan. A standard laboratory text useful in the practice of the immunohistochemical assays of the invention is Harlow and Lane, "Antibodies: A Laboratory Manual" (Cold Spring Harbor Laboratory, New York: 1988), the contents of which are hereby incorporated into the present specification by reference thereto.

This invention is illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

EXAMPLE I

A. Materials and Methods

4-Benzyoylbenzoic acid (eBa) was purchased from Aldrich Chemicals. Bovine serum albumin (BSA), rabbit serum albumin (RSA), ovalbumin (OVA), and N-hydroxysuccinimide were from Sigma Chemical. Dicyclohexylcarbodiimide was from Fluka. Cyclosporin A (CsA), [$^3$H]CsA (SOCi/mMole), Cyclosporin "RIA-kits" and the various modified derivatives were generous gifts from Sandoz Ltd., Basel, Switzerland. [$^3$H]CsA (17Ci/mMole) was purchased from Amersham. Kieselgel (silica gel 60 F254) was purchased from E. Merck (cat. no. 5766).

B. Photolysis reaction

CsA (104 mg, 83 μmoles) was mixed with 36 mg (160 μmoles) of BBa in 0.6 ml of benzene. The solution was purged with nitrogen gas and photolyzed at 320nm with a Spectroline B100 UV lamp (Spectronics, Westbury, L. I.) for 7 hours at a distance of 8 cm, at room temperature. Approximately 1 microcurie of [$^3$H] dihydro CsA was added as a tracer prior to exposure to UV. After photolysis, the benzene was evaporated in a rotating still in vacuo and the dried produce dissolved in 1.5 ml of methanol. The product was isolated by preparative thin layer chromatography on silica gel, in a solvent system of $CHCl_3$/methanol (85/15). Two major bands wee seen: Rf=0.58 and 0.72. The slower moving band (i.e. the product of the reaction, CsA-BBa) was eluted with methanol, and counted for radioactivity.

C. Hapten-Protein Conjugate

CsA-BBa (5.5 mg, ca. 4 μmoles) was added to 1 ml solution containing 552 μg (4.8 μmoles) of N-hydroxysuccinimide (NHS) and 825 μg (4 Amoles) of dicyclohexylcarbodiimide in 1 ml of methanol. The reaction was allowed to run overnight at room temperature and ester formation was detected with a neutral Fe-hydroxanate test (10–11).

Carrier proteins (BSA, RSA, or OVA) (10 mg; 0.14 μmole) were dissolved in 1.0 ml of distilled $H_2O$, and the pH adjusted to 9.0 with M $Na_2CO_3$. CsA-BBa-NHS (5.2mg; 3.6 μmoles) in 1.0 ml of methanol was added dropwise to the protein solution. After all was added, the pH was readjusted to 9 and the reaction allowed to proceed overnight at room temperature. The reaction mixture was then dialyzed against PBS for 24 hours and counted for radioactivity to determine coupling efficiency. About 6–7 cyclosporins were coupled to each molecule of BSA, RSA, or OVA. The conjugates were further purified by gel filtration HPLC (LKB TSK 3000). Confirmation of the linkage of CsA to the proteins came from RIA inhibition experiments. Quantitation is not possible by this technique because there was no way to determine the valence of the conjugate as a competitive inhibitor, i.e., how many of the haptens linked to the protein took part in the inhibition reaction.

D. Other CyA-BBa Derivatives

The following amide derivatives of CyA-BBa, ethanolamide, monoamino-hexanediamine, amide of D-Lysine methyl ester, D-glucamide, and stearylamine were produced using the same methods above and the methods of example III by reacting ethanolamine, hexanediamine, D-lysine-O-methyl ester, and octadecialamine, respectively, with N-hydroxysuccinimide ester of CyA-BBa.

E. Immunization

Two female New Zealand White rabbits were immunized intradermally along with the back, with a 1:1 (v:v) mixture of CsA-BBa-BSA in complete Freund's adjuvant (1 mg/ml of antigen). The rabbits were boosted with CsA-BBa-BSA in incomplete Freund's adjuvant at 3–4 week intervals and bled weekly following each boost. Both rabbits responded by producing cyclosporine-specific antibodies. The sera of one rabbit, R575, was characterized further.

F. Radioimmunoassay

Serum antibodies were detected by a modification of the published radioimmunoassay (5, 12). Serum (100 μl) diluted in Sandoz buffer A (50 mM Tris, pH 8.5) was added to 200 μl of [$^3$H]CsA in Sandoz buffer B (50 mM Tris, pH 8.5; 0.1% Tween 20) containing 2% horse serum, and incubated for 2 hours at room temperature or overnight at 4° C. Binding by diluted preimmune serum was used as a control. Free and bound ligand were separated with charcoal supplied by Sandoz according to their procedure.

G. Determination of antibody specificity

Antibody specificity was determined by an inhibition RIA, using a panel of size CsA analogues, modified at different amino acid positions. The cyclosporin derivatives were dissolved in 100% ethanol at a concentration of 5.0 mg/ml, stored at −20° C., and diluted to final concentrations of 0.27 nM to 2.7 μM in Sandoz buffer B for the inhibition experiments. A constant dilution of rabbit antibody, in buffer A, was added to 200 μl of buffer B containing [$^3$H] dihydro CsA and different amounts of inhibitor, and incubated overnight at 4° C. Inhibition curves for each CsA derivatives were generated.

H. Detection of CsA in sera of transplant patients

Cyclosporin levels in the sera of 25 transplant patients were determined by an inhibition RIA, using either our rabbit anticyclosporin antibodies diluted 1:600 or a polyclonal antibody preparation supplied by Sandoz, as part of their kit. Diluted rabbit anticyclosporin antiserum (100 μl) or Sandoz polyclonal antibody were added to 100 μl [3H]CsA in buffer B and 100 μl of patient's serum prediluted either 1:5 (for Sandoz antibody) or 1:15 (for our rabbit antibody) in buffer B, containing 2% horse serum. Sera from three different patients, taken before they had begun cyclosporin treatment, were used as controls. Samples were incubated overnight at 4° C., and CsA levels were calculated by comparing the level of inhibition to a standard curve obtained with known amounts of cyclosporin.

I. Scatchard Analysis

The binding constant of the rabbit antibodies was determined by Scatchard analysis. Different concentrations of [$^3$H] dihydro CsA, ranging from 10 nM to 0.1 nM, were added to a constant amount of antibody and allowed to incubate overnight at 4° C., bound ligand was determined by the RIA described above.

Results

Figure 1:
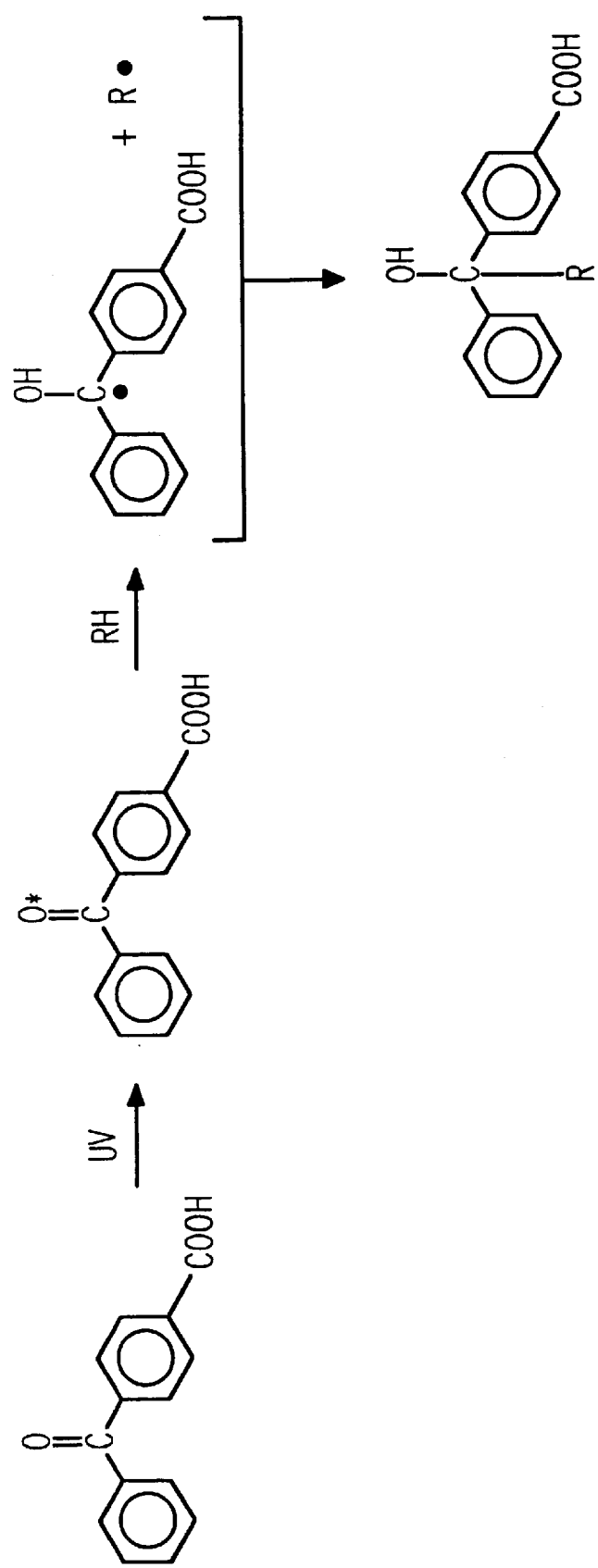
FIG. 1. Photochemical reaction between CsA and BBA.

CsA lacks chemically active groups that can be used for conjugation to proteins. Therefore, a novel procedure was developed for the purpose of introducing carboxyl groups into the molecule. This procedure, photochemical in nature, inserts a carboxyl-containing molecule (BBa) into the alkyl side chains of CSA (FIG. 1), presumably but not certainly, at random.

Figure 2:
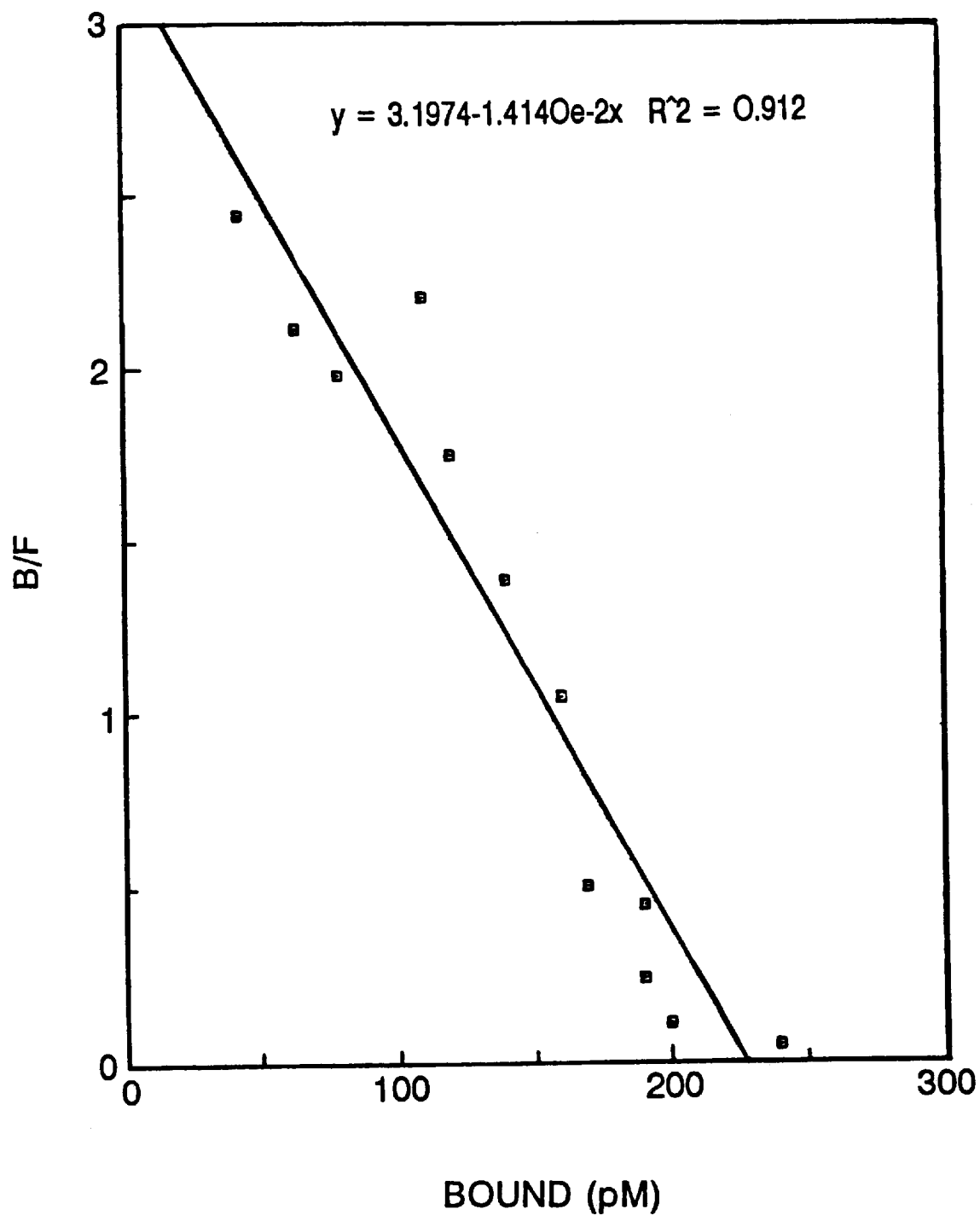
FIG. 2. Scatchard plot of binding data.

Antibodies generated in rabbits with the CsA-BBa-BSA conjugate were examined for specificity and affinity by RIA. Scatchard analysis (FIG. 2) revealed a relatively homogenous population of high affinity antibodies, with Kd–9.8±2.8×10$^{-11}$M.

Figure 3:
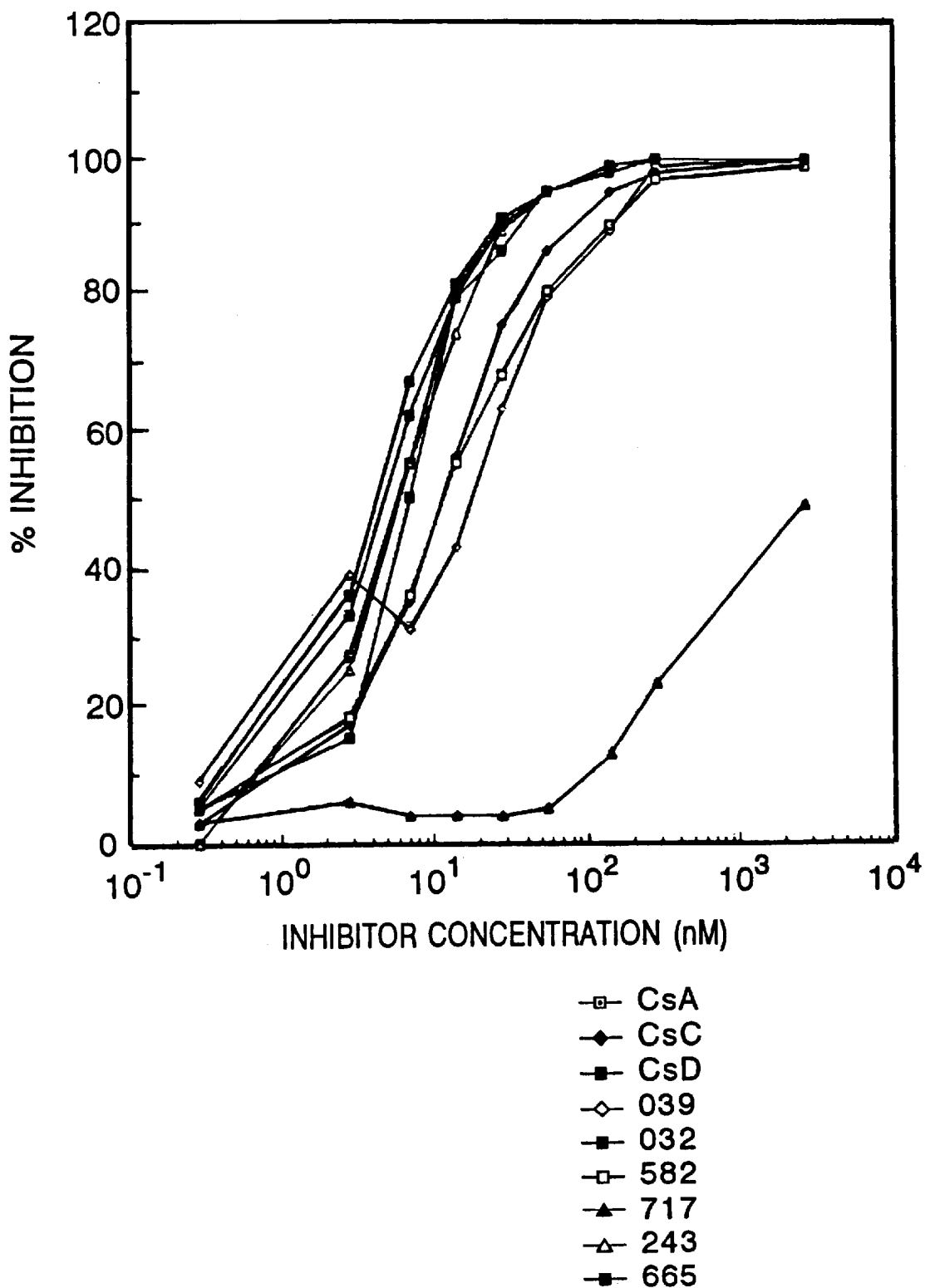
FIG. 3. Inhibition of the binding CsA to R575 by various cyclosporine derivatives.

The specificity of the antibodies for various cyclosporin derivatives was determined by an inhibition RIA. The results are shown in FIG. 3 and Table I. The derivatives can be divided roughly into three groups according to their affinities: CsA, CsD, 665, 243 and 032 are in the high affinity group. CsC, 582 and 039 are of moderate affinities; 717 inhibits very poorly.

Figure 4:
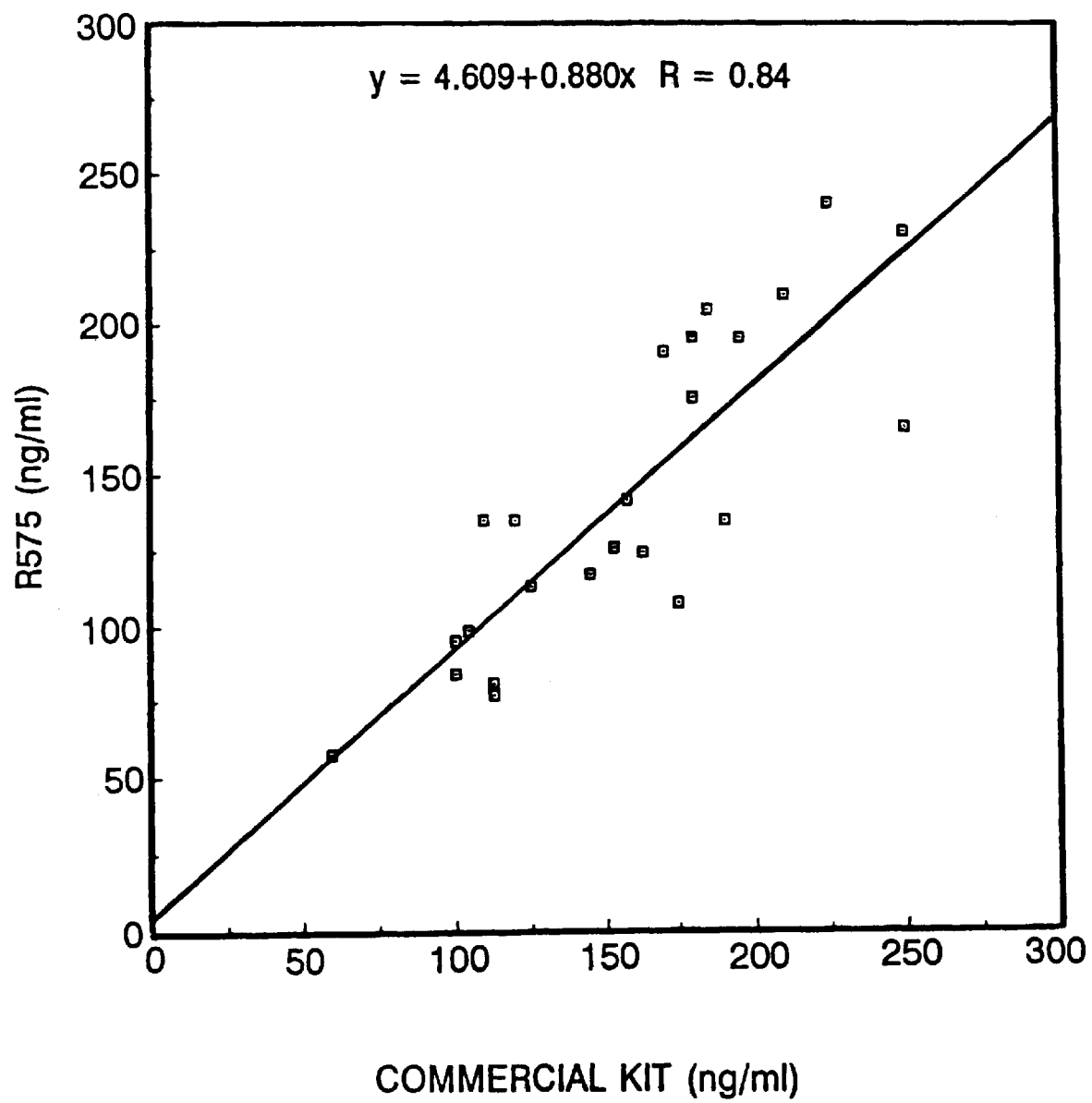
FIG. 4. Titers (ng/ml) of patients' sera as determined by RIA using R575 and Sandoz antibody.

Shown in Table II are the results of assays of cyclosporin levels in the sera of patients undergoing CsA treatment subsequent to cardiac transplantation. Titers were determined using our antibodies and the polyclonal antibodies in the Sandoz kit. Also tabulated in Table II are data supplied by the laboratory of the Department of Surgery. As illustrated in FIG. 4, in our hands the levels determined with our antibody agreed with results using the commercial kit. Linear regression of analysis of the data yields a slope of 0.88 and a correlation coefficient of 0.84.

Discussion

The α, β unsaturated ketone, BBa, is among reagents that, upon photoactivation by U.V. light, can insert into aliphatic side chains (7). It was selected for this study because its photoactive intermediate does not cleave peptide bonds (13). This is an important consideration because it has been shown that a single break in a peptide bond of CsA, such as in iso-CsA, which has lost a peptide bond by an N O shift, leads to loss of activity even though, in the case of Iso-CsA, a cyclic structure is maintained. Apparently an altered conformation leads to a biologically inactive molecule.

The insertion of BBa into CsA is probably a somewhat random process, although we have not attempted to characterize the various products. If random, we are generating populations of antibodies that recognize different residues of the CsA molecule. We have tried to learn something about these antibodies by doing inhibition studies with a panel of cyclosporin derivatives (FIG. 3, Table I). First of all, the relatively shallow slopes of the curves indicate that the immune response is oligo or polyclonal, probably the former. If it were monoclonal, 90% inhibition would occur at a tenfold higher concentration than 10% inhibition. A second important observation is that 100% inhibition of [$^3$H] CsA binding can be obtained with all of the competing cyclosporin derivatives except 717, which, however, is certainly capable of more than 50% inhibition. These results indicate that all of the cyclosporin derivatives compete for the total population of antibodies specific for CsA.

The inhibition data in Table I and FIG. 3 indicate that the various cyclosporine derivatives can be divided into three groups with respect to their affinities for the population of antibodies in the immune sera. CsA, CsD, 665, 243 and 032 bind best. Moderate affinities are shown by CsC, 582 and 039. The results with 717 indicate low affinity. Derivative 717 differs from CsA by having a bulky O-t-butyl-D-serine of D-alanine at position 8. This could implicate position 8 as a dominant epitope. On the other hand, introduction of a bulky group at position 8, in place of the compact methyl group of D-alanine, could distort the cyclosporine molecule markedly (6).

The derivatives showing moderate affinities, CSC, 582 and 039, are substituted at position 2, 3 and 6 respectively.

TABLE 1

IC$_{50}$[a] of Various Analogues of CsA

| Derivative[b] | IC$_{50}$ (nM) |
|---|---|
| CsD | 4.3 |
| 665 | 4.8 |
| A | 6.0 |
| 243 | 6.0 |
| 032 | 7.0 |
| CsC | 11.5 |
| 582 | 12.0 |
| 039 | 18.0 |
| 717 | 2700 |

[a]IC$_{50}$ = Concentration for 50% inhibition
[b]The derivatives listed differ from CsA in the following ways: CsD, valine replaces α-aminobutyric acid at position 2;
665, 0-acetylthreonine replaces α-aminobutyric acid at position 2;
243, hydroxyl group of (4R)-4-[(E)-2-butenyl]-4-N-dimethyl-L-threonine in position 1 is acetylated;
032, N-methyl-isoleucine replaces N-methylvaline at position 11;
CsC, threonine replaces α-aminobutyric acid at position 2;
582, proline replaces sarcosine at position 3;
039, N-methyl-D-alanine N-methylleucine at position 6;
717, 0-t-butyl-D-serine replaces D-alanine at position 8.

TABLE 2

Cyclosporine Titers in Patients' Sera (ng/ml)

| Hospital Patient # | R575[a] | Commercial[b] | Laboratory[c] |
|---|---|---|---|
| 1 | 51 | undetectable | 30 |
| 2 | 190 | 170 | 128 |
| 3 | 195 | 180 | 156 |
| 4 | 135 | 120 | 76 |
| 5 | 175 | 180 | 180 |
| 6 | 135 | 110 | 88 |
| 7 | 195 | 195 | 164 |
| 8 | 205 | 185 | 172 |
| 9 | 240 | 225 | 245 |
| 10 | 210 | 210 | 215 |
| 11 | 113 | 125 | 180 |
| 12 | 95 | 100 | 124 |
| 13 | 77 | 113 | 124 |
| 14 | 98 | 105 | 88 |
| 15 | 84 | 100 | 112 |
| 16 | 124 | 163 | 152 |
| 17 | 165 | 250 | 205 |
| 18 | 135 | 190 | 180 |
| 19 | 141 | 158 | 132 |
| 20 | 231 | 250 | 188 |
| 21 | 126 | 153 | 134 |
| 22 | 81 | 113 | 88 |
| 23 | 117 | 145 | 110 |
| 24 | 107 | 175 | 148 |
| 25 | 57 | 60 | 71 |

[a]Antibodies prepared as described above.
[b]Antibody from kit from Sandoz, Ltd. Assay run in our laboratory.
[c]Results reported by hospital laboratory using Sandoz Kit.

None of the substitutions are bulky. However, the substitution of proline for sarcosine at position 3 is known to disturb the conformation of 582 at positions 3 and 4 (14).

Those derivatives having affinities similar to that of CsA are substituted in positions 1, 2 and 11, all clustered at one "face" of the cyclic peptide. The substitutions, however, are not drastic with respect to size differences of the side chains. A definitive study of the specificity of the antisera and correlation with conformation and biological activity requires testing with a larger number of cyclosporin analogues, which are available (14).

Assay of cyclosporin levels in patients' sera is feasible with this antibody preparation. Our results (FIG. 4 and Table II) are in good agreement with cyclosporin levels determined using commercial (Sandoz) antisera prepared by immunization with a protein conjugate of CsC. The moderate discrepancies probably indicate differences in cross specificities of the antibodies for metabolites of cyclosporine, (5), which is to be expected since our antigen differs from the antigen used to produce the commercial antiserum.

EXAMPLE II

Preparation of CyA-BSA Conjugate and CyA-Sepharose Affinity Column

The character of the side chains of CyA (i.e., an absence of amino or carboxyl groups) precluded the use of conventional coupling procedures, except possibly to the unusual "C-9-amino acid" in position 1(N-methyl-(4R)-4-butenyl-(L)-threonine) (15–17). However, modification of this amino acid was ill advised since this residue was critical to the biological activity of CyA. CyC has threonine instead of τ-aminobutyric acid at the second amino position (AA2). This analog is biologically active and has been used to prepare cyclosporine-protein conjugates using the hemisuccinate derivative (15, 5). As noted by Kahan, however, coupling to this residue was likely to lead to stearic interference with the "active" portion of the molecule (18). This conclusion was based on substitution studies in which it had been shown that amino acids 11, 1, 2, and 3 were critical for immunosuppressive activity (17). Because of this possibility, we used a photochemical procedure that has provided random links to the various exposed methyl or methylene groups of CyA. By having populations of CyA derivatives heterogeneous with regard to attachment sites, it was insured that a portion of the molecules could be coupled to protein without the active amino acids being buried.

We first reacted p-nitrophenyl-2-diazo-3,3,3-trifluoropropionate (19, 20) with a large excess of aminohexanoic acid in anhydrous dimethyl formamide. The reaction mixture was incubated in the dark at room temperature for 18 hours, following a similar procedure described by Samuels and coworker (21). The product was operated by preparative TLC (21) and has the following formula:

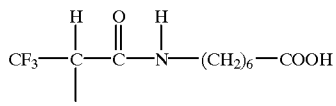

Next CyA, which is very soluble in all organic solvents except hexane (17), was mixed with the above product in a benzene solvent and photolyzed. Two moles of carbene precursor to one mole cyclosporine A were also used. The mixture was irradiated with UV light from a mercury arc (mainly 254 nm). Reaction conditions were empirically chosen to avoid multiple substitutions of CyA molecules. Derivatized CyA (CyA-Hex) were separated by TLC. To provide a functional group that reacted with amino groups, the carboxyl group(s) of CyA-Hex were activated by conversion to the N-hydroxy succinimide (NHS) ester in the presence of dicyclohexylcarbodiimide. Then, CyA-Hex-NHS was dissolved in anhydrous dimethyl formamide and added as a small volume to bovine albumin and keyhole limpet hemocyanin in pH-8.8 bicarbonate buffer and incubated overnight at 4° C. These conditions have been found to work well with other NHS derivatives (22, 23). To determine the degree of substitution of protein amino acid groups by CyA-Hex, we used the trinitrobenzene sulfonic acid procedure of Habeeb (24). In our previous studies, ESA and KLH conjugates were both found to work well as immunogens and as antigens in solid phase immunoassays. All chemicals needed for the preparation of these reagents were commercially available.

To prepare a CyA affinity column, an excess of CyA-Hex-NHS in anhydrous dimethyl formamide was reacted with aminohexyl-Sepharose 4B (AH-Sepharose 4B), suspended and swollen in the same solvent. This matrix, which was prepared by a carbonyldiimidazole coupling procedure, avoided the introduction of the ion exchange groups associated with the frequently used cyanogen bromide coupling and reduced leakage due to the cross-linked agarose and the stable carbonyldiimidazole linkage (25). Trinitrobenzene sulfonic acid will be used to get a semiquantitative estimate of residual amino groups on Sepharose beads.

EXAMPLE III

A. Production and Characterization of Nonoclonal Antibodies

The production and characterization of monoclonal antibodies specific for Cyclosporine A has previously been reported in Cacalano et al., *Mol. Immunol.*, Vol. 29, pages 107–118 (1991), the entire contents of which are hereby incorporated by reference.

1. Reagents

Figure 5B:
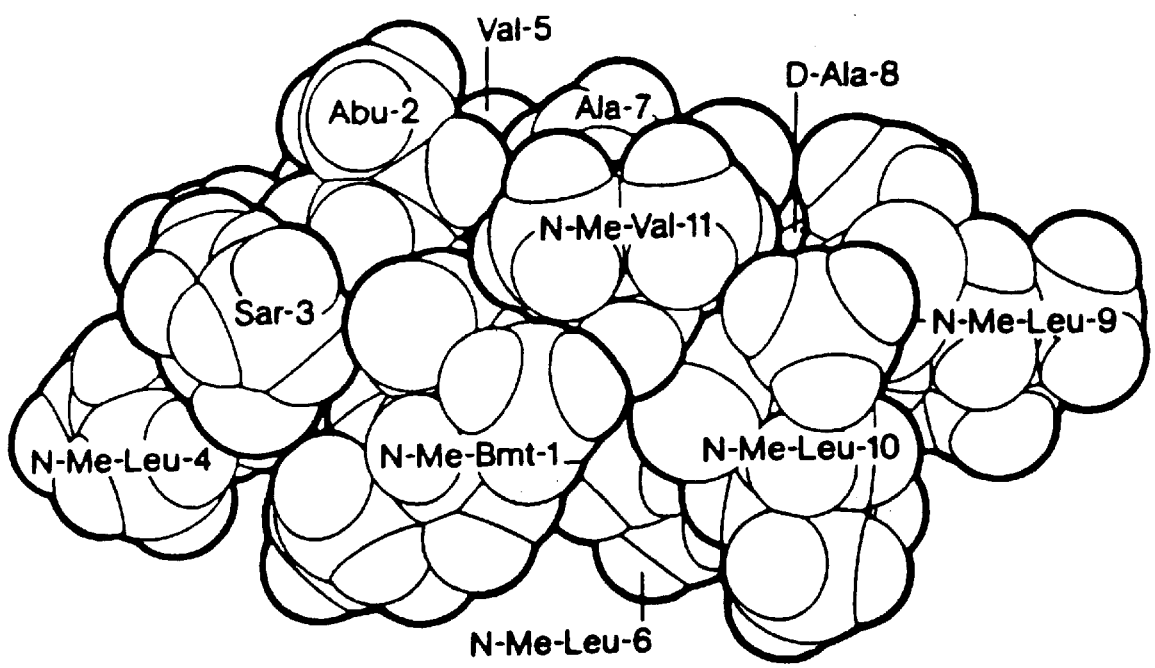

Cyclosporine A (Cs, Sandimmune), and the various modified Cs derivatives, including CsC, 665, 032, 243, 582, 039, and 717 were obtained from Sandoz Ltd. Basel, Switzerland. The structural diagram and space-filling model of Cs are shown in FIG. 5B. Structural information for the Cs derivatives is as follows: CsC, threonine replaces α-aminobutric acid at position 2: 582, proline replaces sarcosine at position 2; 665. 0-acetyl threonine replaces α-aminobutyric acid at position 2; 243, hydroxyl group of (4R)-4-[(E)-2-butenyl]-4-N-dimethyl-L-threonine at position 1 is acetylated; 032, N-methylisoleucine replaced N-methyl-valine at position 11; 039, N-methyl-D-alanine replaces N-methyl isoleucine at position 6; 717, 0-t-butyl-D-serine replaces D-alanine at position 8.

[$^3$H]CsA (17 Ci/mmol) was purchased from Amersham Corp., (Arlington Heights, Ill.). 4-Benzoylbenzoic acid (BBa) was purchased from Aldrich Chemicals (Milwaukee, Wis.). Bovine serum albumin (BSA), ovalbumin (Ova), and polyethylene glycol (PEG) 8000 were from Sigma Chemical Corp. (St. Louis, Mo.). Bovine gamma globulin was purchased from Mann Research Laboratories, Inc. (New York, N.Y.). Dextran G10 was from Pharmacia LKB Biotechnology (Upsala, Sweden). Norit A (charcoal) was purchased from Fisher Scientific (Springfield, N.J.). Fetal calf serum (FCS) was from Hyclone (Logan, Utah). Peroxidase-conjugated goat anti-mouse IgG+IgM was purchased from TAGO (Burlingame, Calif.). Purified human liver cyclophilin (CyP) was a generous gift from Dr. Robert E. Handshumacher, Yale University. The monoclonal antibody isotyping kit was from Zymed (San Francisco, Calif.).

2. Hybridomas

The Cs photolysis reaction with BBA, purification of Cs-BBa, and conjugation of Cs-BBa to BSA and Ova have been described previously (Cacalano et al., 1989). BALB/c mice (Charles River) were immunized i.p. with approximately 0.10 mg of Cs-BBa-BSA emulsified in CFA. Mice were boosted at three week intervals with 0.1 mg Cs-BBa-BSA emulsified in incomplete Freund's adjuvant (IFA), over a period of six months. Three days before fusion, mice were injected i.v. with 50 μg of Cs-BBa-BSA in PBS. Spleen cells were fused with nonsecreting myeloma cells P3×63-AgS.653 (Kearney et al., 1979), according to the method of Sharon et al. (1979). Two weeks later, the hybridoma supernatant was assayed for the presence of anti-cyclosporine antibodies by ELISA (see below). The ELISA positive clones were confirmed for Cs binding in radioimmunoassay. Clones positive by RIA were subcloned twice by limiting dilution. The class and subclass of each antibody were determined by ELISA.

3. ELISA for anti-Cyclosporine Monoclonal Antibody screening

Polystyrene microplates (Corning 25855) were coated with 500 ng/ml Cs-BBa-Ova in 0.1 M sodium bicarbonate, pH 9.3, overnight at 4° C. Plates were washed with PBS containing 0.1% Tween 20 (PBS-Tween), an 150 μl of culture supernatant were incubated in the wells for 1 hr at 37° C. Plates were washed four times with PBS-Tween, and 1/3000 dilution of horseradish peroxidase-labeled goat anti-mouse IgG+IgM in PBS-Tween was added to each well. After washing the plates four times with PBS-Tween, 150 μl of substrate (7 mg o-phenylenediamine dihydrochloride in 10 ml of 0.1 M citrate-phosphate buffer, pH 4.8, containing 5 μl of 30% $H_2O_2$) was added. The reaction was stopped after 10 mins by the addition of 50 μl 8 N $H-SO_4$, and the absorbance of each well was measured at 490 nm on a Dynatech Microplate reader.

A second ELISA Procedure used conjugates of D-Lys$^8$-Cs-BSA and Thr$^2$-Cs-BSA for coating (Queeniaux et al., 1987b). An indirect detection system consisting of rabbit anti-mouse Ig followed by alkaline phosphates-conjugated goat anti-rabbit IgG was performed as previously described (Queenlaux et al., 1987b).

4. Compatities of Monoclonal Antibodies with cyclophilin

Polystyrene microplates were coated with 500 ng/ml of Cs-BBA-Ova in 0.1 M $NaHCO_3$, pH 9.3, overnight at 4C. Hybridoma supernatant was diluted in 0.1 M $Na-PO_4$, pH 7.0. Cyclophilin was added to final concentration of $1.6 \times 10^{-7}$ M–$1 \times 10^{-11}$ M, and incubated in the microtiter wells for 1 hr at 37° C. Bound McAbs were detected as described above. The results were expressed as percentage of inhibition in the presence of CyP, relative to the O.D. 490 nm measured in the absence of CyP.

5. Radioimmunoassay

For McAb screening, 100 μl of hybridoma supernatant was added to 100 μl of RIA buffer B (50 mM Tris, pH 6.5 containing 0.1% Tween 20) and 100 μl buffer B containing [$^3$H]Ca (final concn 1 nM) and incubated for 2 hr at room temp or overnight at 4° C.

Bound was separated from free [$^3$H]Cs by the addition of 150 μl Sephadex C10-coated charcoal (Norit A) in RIA buffer A (50 mM Tris, pH 8.5), incubated for 12 min at 4° C., followed by centrifugation. The supernatant, containing bound [$^3$H] Cs, was counted for radioactivity.

For Scatchard analyses of high affinity antibodies, 100 μl of diluted hybridome supernatant was incubated with [$^3$H] CsA at concns from $1.0 \times 10^{-5}$M to $5.0 \times 10^{-11}$ M, overnight at 4° C. Bound from free [$^3$H]Cs was separated by incubation with dextran coated charcoal as described above.

For Scatchard analyses of low affinity antibodies, diluted hybridoma supernatant was incubated with [$^3$H]Cast concs of $5'10^{-5}$ M–$5 \times 10^{-10}$M over night at 4° C. Bound from free [$^3$H]Cs was separated by the addition of 50 μl of a 10 mg/ml solution of bovine gamma globulin in buffer A, followed by the addition of 200 μl of 30% PEC 8000 in buffer A, vertexing and incubating for 10 min at 4° C. Tubes were centrifuged for 10 min and the pellets were redissolved in 500 μl distilled $H_2O$ and counted for radioactivity.

B. Results

Of the 2 McAbs generated, 1E are IgGl, K, B9 1.2 is IgG2b, k and A11 2.10, G2, 2.1, and B-1 1.4 are IgM, k.

The McAs were first characterized as to epitope specifically in an ELISA, with Cs-BBA-ovalbumin as the coating antigen, Cs, Cs-BBa (the immunizing hapten), or one of seven Cs analogs, singly substituted at different amino acid residues was examined for inhibition.

Figure 6A:
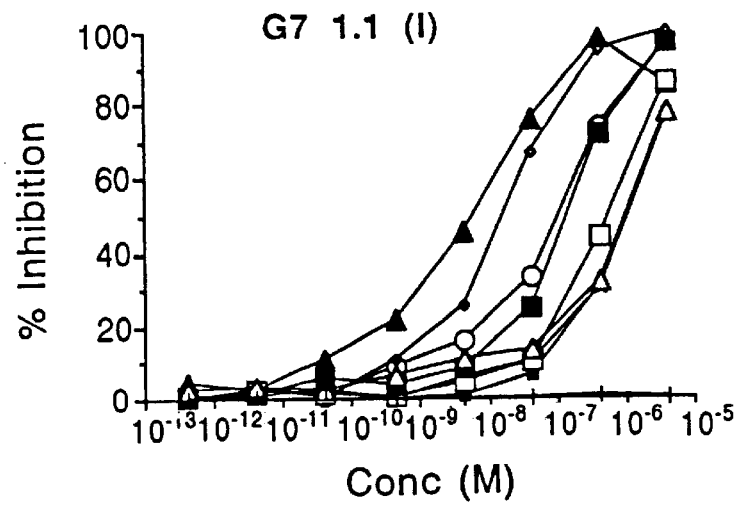
FIGS. 6A–6E. ELISA inhibition curves for one representative of each of the specificity groups defined in the Experimental Details Section. Conditions of the assay are also described therein. The CsA derivatives used in this study are as follows: CsA (○), CsA-BBa (◊), CsC (■), 582 (□), 665 (▲), 243 (X), 032 (•), 039 (Δ), 717 (+).
Figure 6B:
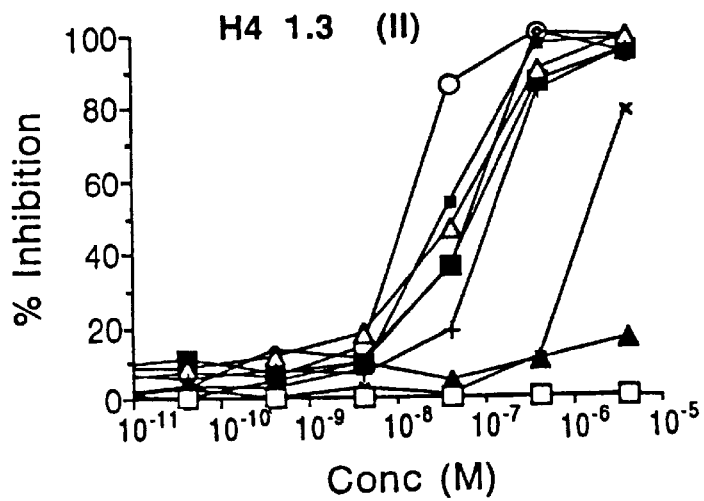
Figure 6C:
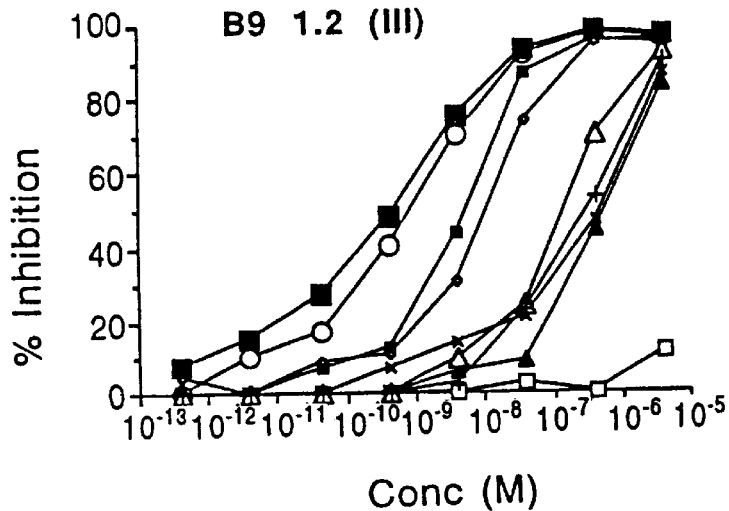
Figure 6D:
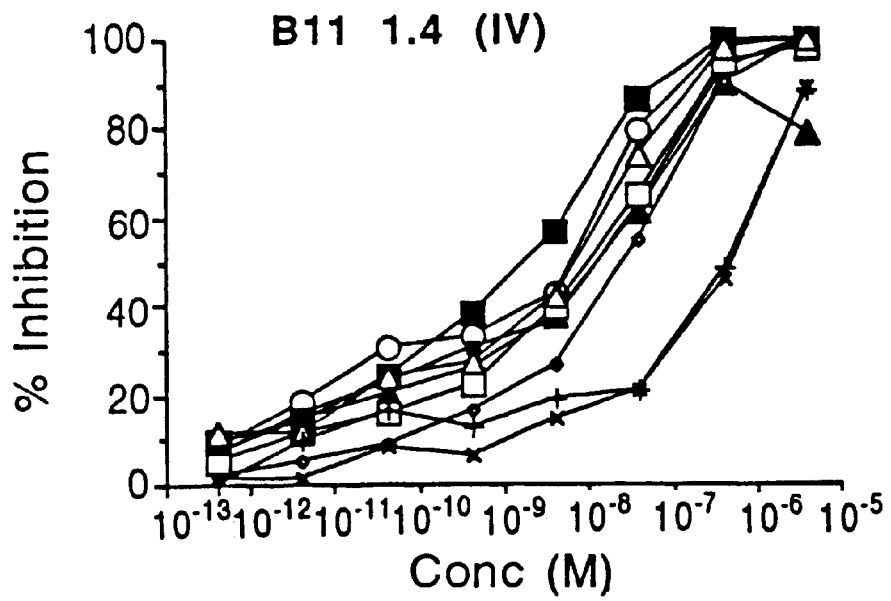
Figure 6E:
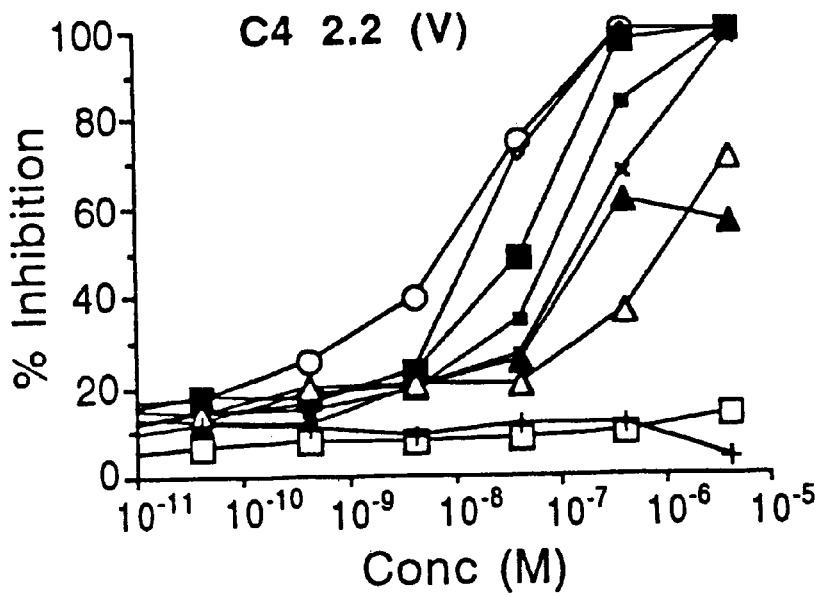
Figure 7A:
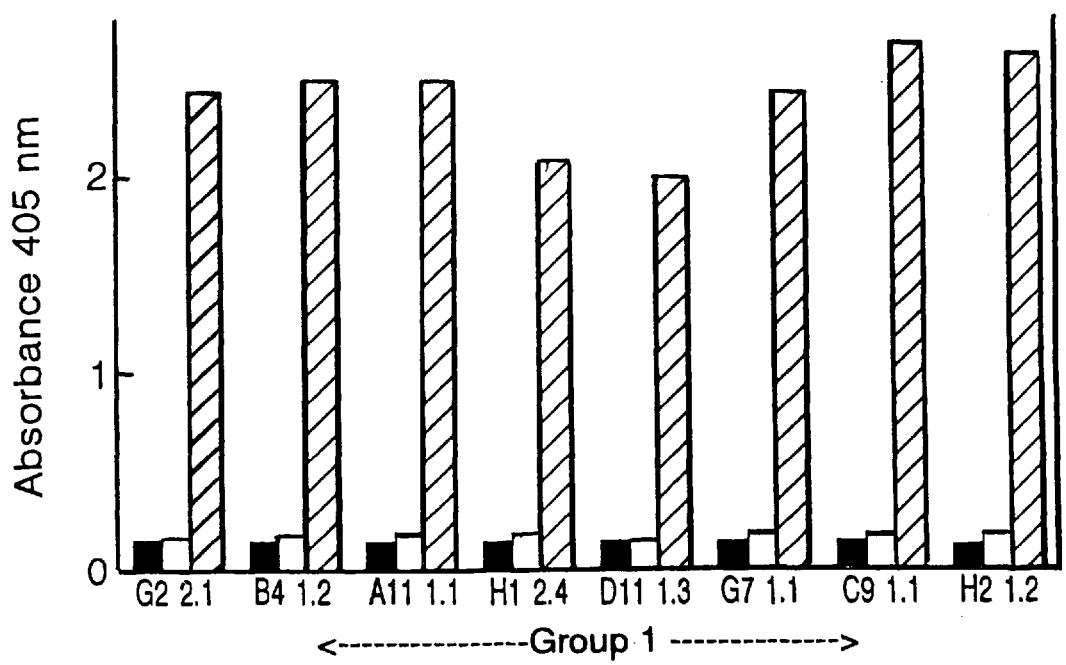
FIGS. 7A–7C. Specific recognition of two opposite regions of the Cs molecule exposed on D-Lys$^8$-Cs-BSA and Thr$^2$-Cs-BSA conjugates by 22 McAbs belonging to the 5 groups of specificity. The D-Lys$^8$-Cs-BSA (□) and Thr$^2$-Cs-BSA (□) conjugates were coated on the solid phase at a concentration of 0.5 μg/ml. Negative control for coating is shown (■). The supernatants of McAb-producing hybridomas were used at dilutions corresponding to the beginning of the plateau of maximum ELISA reaction with the best recognized Cs-BSA conjugate.
Figure 7B:
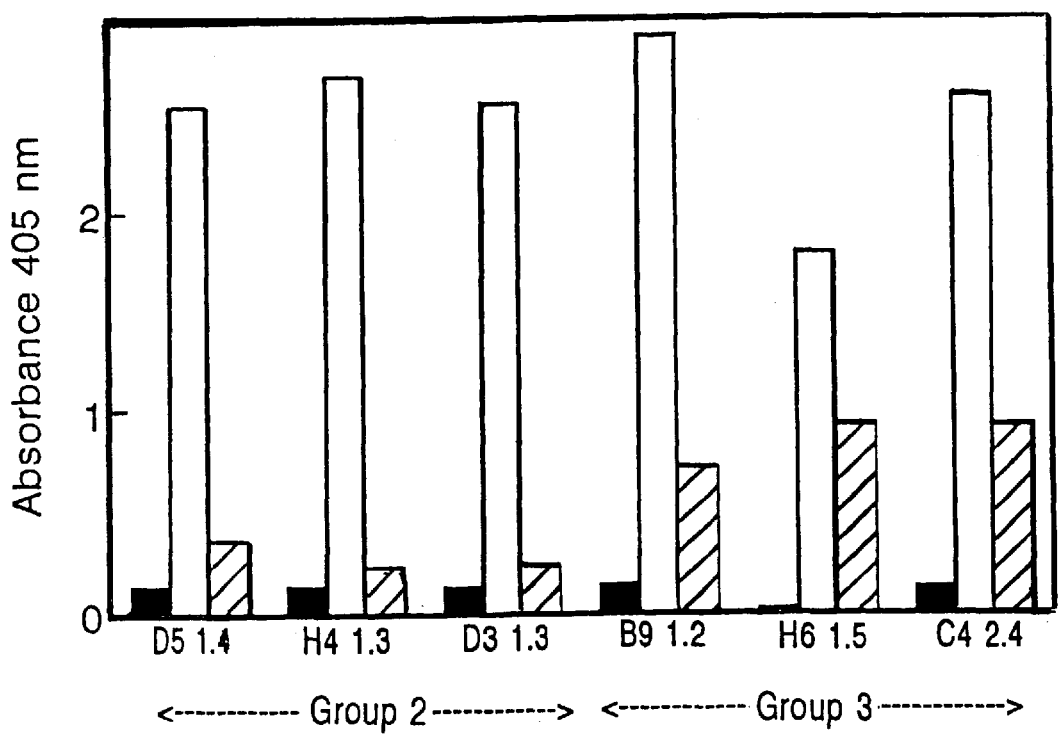
Figure 7C:
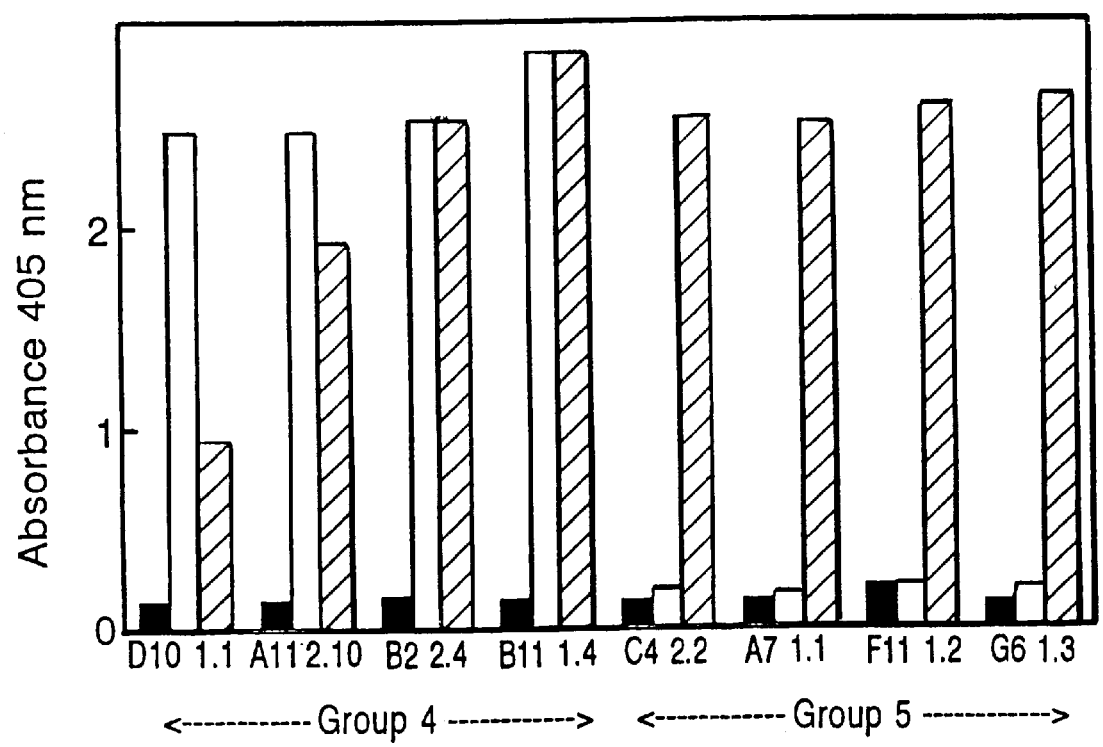
Figure 8A:
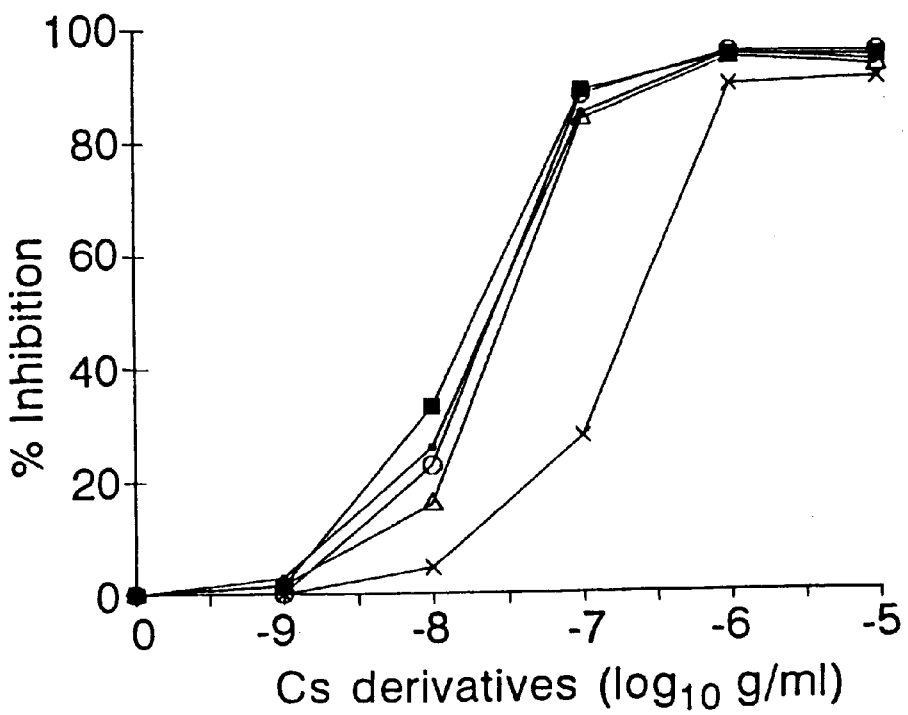
FIGS. 8A and 8B. ELISA inhibition curves of the reaction of McAb B-11 1.4 with D-Lys$^8$-Cs-BSA (FIG. 8 A) and Thr$^2$-Cs-BSA (FIG. 8B) conjugates coated on the solid phase (0.25 μg/ml). The following Cs-derivatives were used as inhibitors: CsA (○), 3'-acetyl-MeBmt-Ce (x), Thr$^2$-Cs (■), MeAla$^6$-Cs (Δ) and MeIle$^{11}$-Cs (•).
Figure 8B:
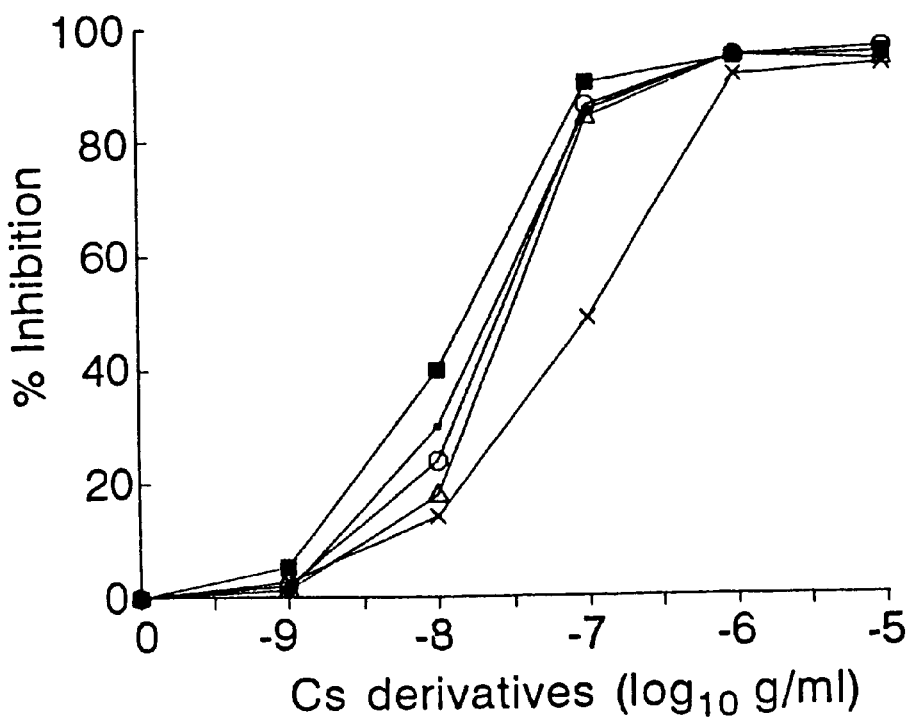
Figure 9:
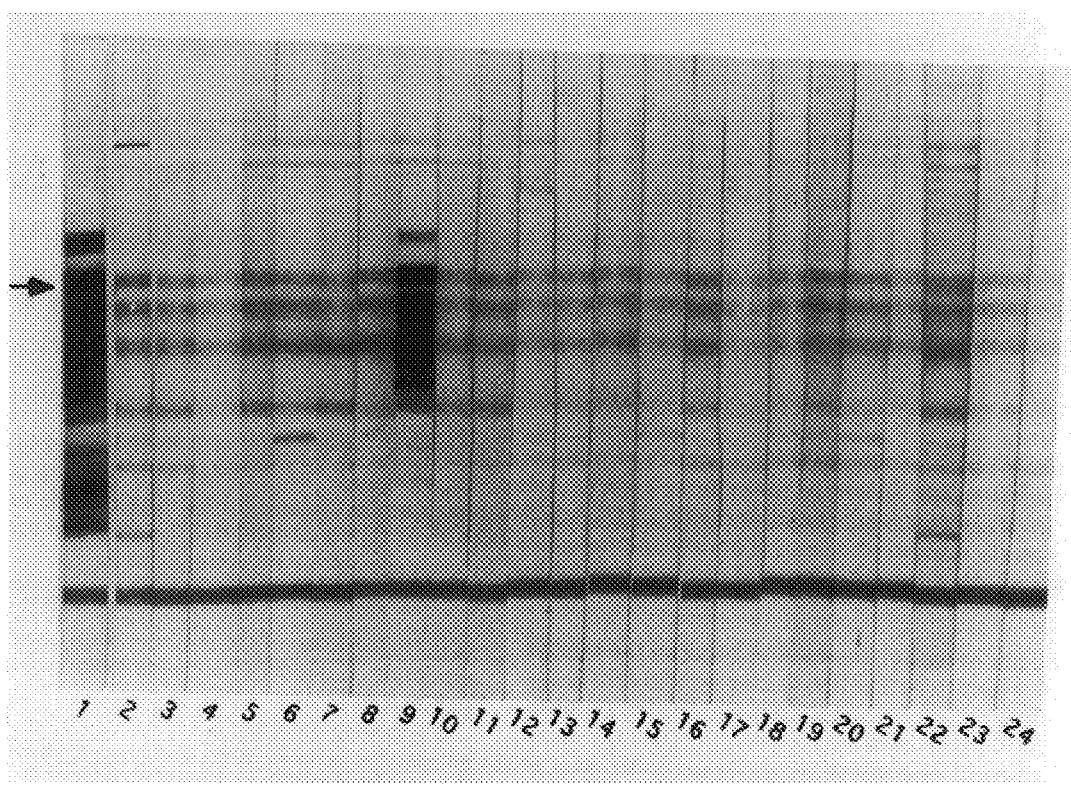
FIG. 9. Western Blot in which Gag of HIV-1 was gel electrophoresed, transferred to a nitrocellulose membrane and cut into strips. Each strip was tested for binding to our various monoclonal anti-CsA antibodies ant to an antibody raised by immunization with Gag (column 1). Column 9 represents action of B-11 1.4. Multiple bands are the results of partion proteolysis of Gag.
Figure 10:
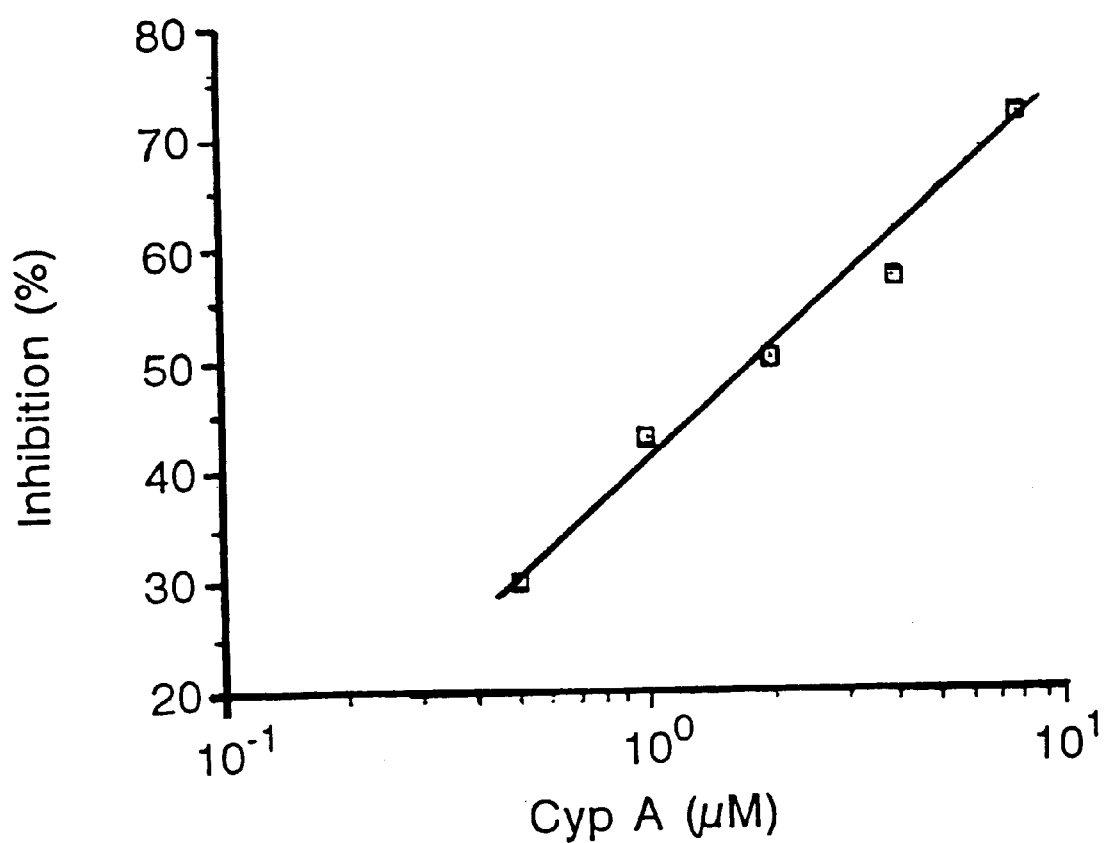
FIG. 10. ELISA in which plate was coated with P24 and competition is seen between cyclophilin A and B-11 1.4.
Figure 11:
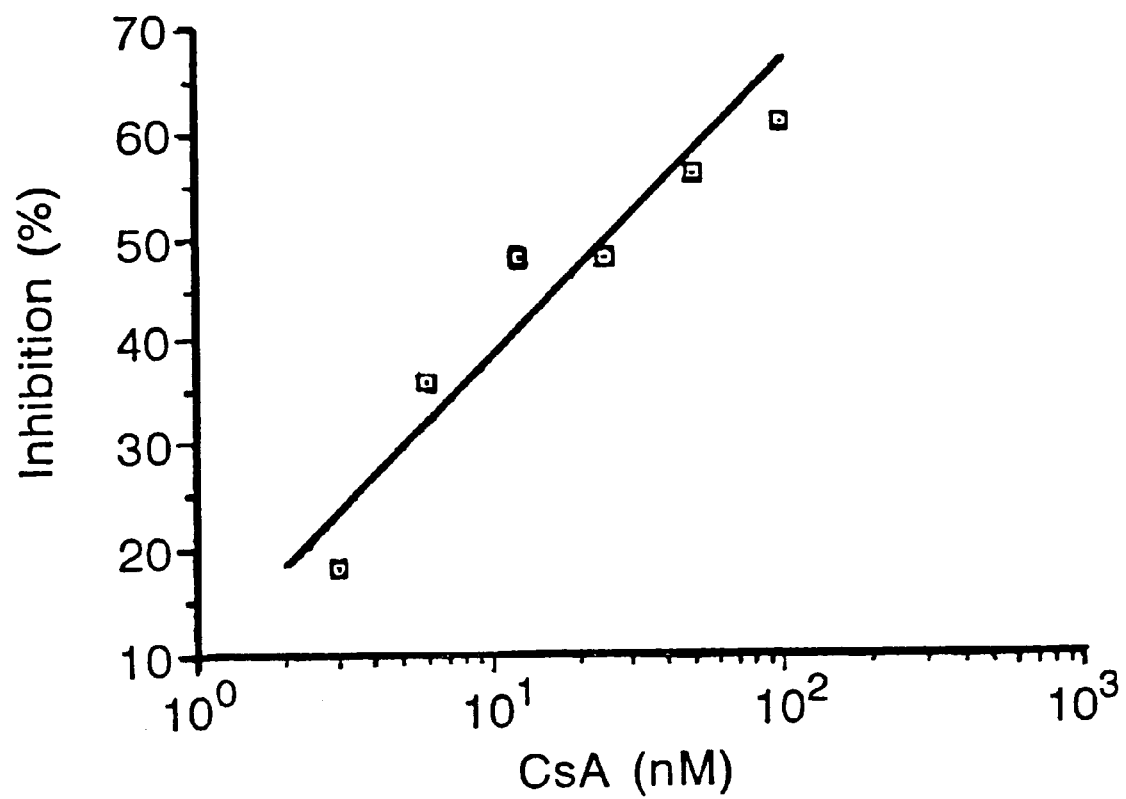
FIG. 11. ELISA in which P24 is used to coat plate and competition is seen between B-11 1.4 and CsA.

A typical set of inhibition of curves is shown in FIGS. 6A–6E. By comparing the relative potencies of the inhibitors, antibody specificity for epitopes on Cs were determined. The antibodies were studied for their sensitivity to the drastically altered IC$_{50}$ as compared to inhibition with Cs. As shown in FIGS. 6A–6B and Table 3, the antibodies can be arranged into five groups, each with uniques binding characteristics. Derivatives giving an IC$_{50}$<50-fold different from unmodified Cs for all members of a group were considered to be modified at a position involved in the contact with the antibody combining site.

Group I contains antibodies that bind to derivative 665, which is modified at position 2 (α-L-aminobutyric acid to O-actylthreonina), with a much higher affinity than they bind to Cs. They are also highly sensitive to the O-t-butyl-D-serine substitution at position 8 in derivative 717, which completely abolishes the inhibitory activity of 717.

The antibodies in group II are sensitive to the substitutions in Cs derivatives 243 (acetylation of hydroxy group of MeBmt at position 1). 665 (O-acetyl threonine in place of α-aminobutyric acid at position 2), and 582 (sarocsine to proline substitution at position 3, which causes a conformational change at positions 3 and 4).

Antibodies in group III are sensitive to the substitutions in Cs derivatives 243, 665, 582, 039, and 717.

Antibodies in group IV are sensitive to the substitution at position 8 in derivatives 717 but are relatively insensitive to other side chain modifications in the Cs derivatives used in the experiment.

Antibodies in group V recognize three derivatives with a much lower affinity than Cs. In the case of derivative 582, the antibody is sensitive to a conformational changes at position 3 and 4, induced by the sarocsine to proline substitution at amino acid 3. They also poorly recognize derivative 039, which contains an N-methylisoleucine to N-methyl-D-alanine substitution at position 6, and are also highly sensitive to the D-Ala to O-t-butyl-D-serine substitution at position 8 in derivative 717.

The binding of the 22 McAbs to D-$Lys^8$-Cs-BSA and $Thr^3$-Cs-BSA conjugates, in which opposite sides of the Cs molecules are likely to be exposed, was analyzed in direct ELISA. As shown in FIGS. 7A–7C, some McAbs could bind selectively to one of the two conjugates, whereas other McAbs bound equally well to both conjugates. For example, all members of groups I and V bound only the $Thr^2$-Ca-BSA conjugate, the McAbs in group II bound only to the D-$Lys^5$-C-BSA conjugate, and Abs in groups III and IV bound both conjugates group III and IV bound both conjugates.

Titrations of hybridoma supernatant on the two conjugates were performed, and the ratio of he McAB concentrations required to achieve similar ELISA reaction with D-$Lys^6$-Cs-BSA and $Thr^2$-Cs-BSA is reported in Table 4. Direct binding of the McAbs to the different Cs conjugates was in agreement with the initial grouping based on the ELISA inhibition studies.

The binding of the 22 McAbs to these two Cs-BSA conjugates was also found to correlate well with their fine specificity patterns, as characterized with a set of 28–36 Cs derivatives. Typical ELISA curves showing McAb binding either to D-$Lys^8$-Cs-BSA (panel A) or to $Thr^2$-Ca-BSA (panel B) and inhibited by Cs or Cs derivatives are shown in FIGS. 8A–8B, D-$Lys^8$-Cs-BSA was subsequently used for coating in the inhibition experiments, except for those McAbs binding selectively to $Thr^2$-Cs-BSA (see Table 4 and FIGS. 7A–7C). An example of the binding of 26 Cs derivatives by McAbs belonging to each of the five specificity groups mentioned above is reported in Table 5. The results are expressed as the difference of $IC_{50}$ (in $\log_{10}$) between the Cs derivatives and Cs. All Cs-derivatives used in this study were selected for having a conserved peptide ring conformation compared with CsA (as determined in NMR or X-ray diffraction).

McAb G71.1 belonging to group 1, was sensitive to substitutions of Cs resides 3, 5, 8 an d9, whereas it did not discriminate between Cs and Cs derivatives substituted at other amino acid positions.

McAb H41.3 (group II) was sensitive to modifications at residues 1–6, indicating that this McAb might recognize a more extended epitope. Within residue 1, this McAb could differentiate between modifications of the first carbon of the McBmt side chain (C3') and modification of the last carbon of this side chain (C8'). When C3', hydroxylated in Cs, was acetylated or dehydroxylated, the $IC_{50}$ for that derivative was >10-fold higher than Cs. In contrast, H41.3 did not discriminate between Cs and Cs-derivatives showing hydroxylation of C8' or missing this last carbon (in Ethyl $MeThr^1$-Cs).

McAb H61.8 (group III) was mostly sensitive to modifications of residues 2, 3, 4, and 6, and also weakly) recognized amino acid 1.

McAb B-11 1.4 (group IV) seemed to have a very different pattern of recognition since only modifications of residues 9 and 10 led to a decrease of binding >10-fold compared to Cs.

McAb C4 2.2 (group V) was sensitive to modifications of residues 2, 6, 8, 9 and 10.

Similar studies were performed with all of the 22 McAbs, using 28–36 Cs-derivatives. It was striking that McAbs from different specificity groups exhibit very different recognition patterns. Within each group, however, the recognitives patterns of the McAbs for the different Cs derivative was strikingly similar. One exception was McAB B9 1.2, which belongs to group III by the first two criteria mentioned above (initial ELISA inhibition with a limited number of Cs derivatives, and binding of both the D-$Lys^8$-Cs-BSA and $Thr^2$-Ca-BSA conjugates), but showed a fine specificity very similar to that of group II McAbs; i.e., it was sensitive to modification of C3' of residue 1, and substitutions of residues 2, 4, 5 and 6.

Based on these results, we can identify residues that are recognized by the different McAbs, as summarized in Table 4, When some substitution at a given residue produced $IC_{50}$ values threshold (+) to greater than tenfold (++) higher than that observed with Cs, it was concluded that the particular residue was important for McAb binding. When all derivatives modified at a given position did not produce significantly different $IC_{50}$ values (−), that amino acid was assumed not interact with the McAb combining site.

TABLE 3

Relative $IC_{50}$[a] values of cyclosporine derivatives for monoclonal antibodies.

| Antibody | CsA | CsC | CsA-BBa | 582 | 665 | 243 | 032 | 039 | 717 |
|---|---|---|---|---|---|---|---|---|---|
| GROUP I | | | | | | | | | |
| G22.1 | 1.0 | 1.0 | 0.1 | 0.25 | 0.007[b] | 9.0 | 2.4 | 9.0 | >1000 |
| B41.2 | 1.0 | 0.9 | 0.0014 | 0.4 | 0.0005 | 10.6 | 1.8 | 3.2 | >1000 |
| H12.4 | 1.0 | 1.2 | 0.05 | 1.3 | 0.004 | 21.7 | 2.4 | 11.2 | >1000 |
| A111.1 | 1.0 | 1.8 | 0.002 | 1.1 | <0.001 | 61.0 | 7.0 | 43.7 | >1000 |

TABLE 3-continued

Relative $IC_{50}{}^a$ values of cyclosporine derivatives for monoclonal antibodies.

| Antibody | CsA | CsC | CsA-BBa | 582 | 665 | 243 | 032 | 039 | 717 |
|---|---|---|---|---|---|---|---|---|---|
| H21.2 | 1.0 | 4.2 | 0.8 | 3.0 | <u>0.2</u> | 68.5 | 3.4 | 10.0 | >1000 |
| C91.0 | 1.0 | 1.3 | 1.3 | 3.6 | <u>0.01</u> | 20.0 | 17.0 | 20.0 | >1000 |
| D111.3 | 1.0 | 1.6 | 0.5 | 1.1 | <u>0.004</u> | 15.0 | 5.8 | 15.0 | >1000 |
| G71.1 | 1.0 | 5.6 | 0.75 | 5.0 | <u>0.02</u> | 13.0 | 11.0 | 16.0 | >1000 |
| GROUP II | | | | | | | | | |
| D31.3 | 1.0 | 25.0 | 0.007 | >10000 | <u>3217</u> | <u>342</u> | 1.0 | 145 | 11.0 |
| D51.4 | 1.0 | 50.0 | 1.0 | >10000 | 10000 | <u>1600</u> | 2.5 | 115 | 115 |
| H41.3 | 1.0 | 6.0 | 6.0 | >1000 | <u>>300</u> | 117 | 2.4 | 4.0 | 8.0 |
| GROUP III | | | | | | | | | |
| C42.2 | 1.0 | 3.2 | 0.2 | >10000 | 5000 | <u>272</u> | 9.0 | >10000 | <u>180</u> |
| H61.5 | 1.0 | 59.0 | ND | >10000 | 1000 | <u>2650</u> | 59 | >10000 | <u>315</u> |
| B91.2 | 1.0 | 2.0 | 11.0 | >1000 | >1000 | <u>>1000</u> | 5.4 | 1000 | <u>222</u> |
| GROUP IV | | | | | | | | | |
| A112.10 | 1.0 | 0.8 | 0.2 | 3.0 | 134 | 84.2 | 2.7 | 1.0 | <u>200</u> |
| D101.1 | 1.0 | 0.9 | 1.4 | 1.5 | 4.3 | 31.0 | 6.7 | 2.7 | <u>75.0</u> |
| B22.4 | 1.0 | 5.8 | 2.1 | 3.5 | 15.8 | 15.0 | 3.0 | 10 | <u>>200</u> |
| B111.4 | 1.0 | 0.4 | 5.0 | 1.5 | 3.0 | 77.0 | 3.0 | 1.0 | <u>72.0</u> |
| GROUP V | | | | | | | | | |
| F111.2 | 1.0 | 2.3 | 2.3 | 1000 | 23.0 | 19.0 | 2.1 | <u>163</u> | >10000 |
| G61.3 | 1.0 | 3.5 | 0.2 | 5250 | 16.0 | 20.0 | 8.0 | <u>165</u> | >10000 |
| C42.2 | 1.0 | 5.6 | 16.0 | >1000 | 46.0 | 76.0 | 12.0 | <u>126</u> | >1000 |
| A71.1 | 1.0 | 2.4 | 0.5 | >100 | 56.0 | 11.0 | 9.0 | <u>>100</u> | >100 |

[a] $IC_{50}$ concentration required for 50% inhibition.
[b] Underlined valued indicate sites of specificity.

TABLE 4

Fine specificity and binding to D-Lys[8]-Cs-BSA and Thr-Cs-BSA conjugates of 22 monoclonal antibodies belonging to groups I–V.

| Group | McAb | | Amino acid residues recognized[a] | | | | | | | | | | Relative binding to BSA-D-Lys[8]-Cs/ BSA-Thr-Cs[b] |
|---|---|---|---|---|---|---|---|---|---|---|---|---|---|
| | | | 1 | 2 | 3 | 4 | 5 | 6 | 7 | 8 | 9 | 10 | 11 | |
| I | G2 | 2.1 | − | − | + + | − | + | − | − | + + | + + | − | − | <0.003 |
| I | B4 | 1.2 | − | − | + + | − | − | + | − | + + | + + | − | − | <0.003 |
| I | A11 | 1.1 | + | − | + + | − | + | + | − | + + | + + | − | − | <0.01 |
| I | H1 | 2.4 | − | − | + + | − | + | + | − | + + | + + | − | − | <0.003 |
| I | D11 | 1.3 | + | − | + + | − | + | + | − | + + | + + | − | − | <0.1 |
| I | G7 | 1.1 | + | − | + + | − | + | + | − | + + | + | − | − | <0.02 |
| I | C9 | 1.1 | − | − | + + | − | − | + | − | + + | + + | − | − | <0.03 |
| I | H2 | 1.2 | − | − | + + | − | + | + | − | + + | + + | − | + | <0.003 |
| II | D5 | 1.4 | + | + | + + | + + | + + | + + | − | − | − | − | − | >50 |
| II | H4 | 1.3 | + + | + + | + + | + + | + + | + + | − | − | − | − | − | >50 |
| II | D3 | 1.3 | + + | + + | + + | + | + + | + + | − | − | − | − | − | >50 |
| III | B9 | 1.2 | + + | − | + + | + + | + + | + + | − | − | + | − | − | 20 |
| III | H6 | 1.5 | + | + + | + + | + + | − | + + | − | − | − | − | − | 3 |
| III | C4 | 2.4 | − | + | + + | + + | − | + + | − | − | − | − | − | 5 |
| IV | D10 | 1.1 | − | − | − | − | − | − | − | − | + + | + | − | 2 |
| IV | A11 | 2.10 | + | − | − | − | − | − | − | + | + + | + + | − | 2 |
| IV | B2 | 2.4 | − | − | − | − | − | − | − | − | + + | + | − | 2 |
| IV | B11 | 1.4 | + | − | − | − | − | − | − | − | + + | + + | − | 2 |
| V | C4 | 2.2 | − | − | + + | − | − | + + | − | + + | + + | + + | − | <0.02 |
| V | A7 | 1.1 | − | − | + + | − | − | + + | − | + + | + + | + + | + | <0.001 |
| V | F11 | 1.2 | − | − | + + | − | − | + + | − | + + | + + | + + | − | <0.06 |
| V | G6 | 1.3 | − | − | + + | − | − | + + | − | + + | + + | + + | − | <0.02 |

[a] + +, + and − correspond to residues strongly, weakly and not recognized by the McAbs as defined in FIG. 6 and Table 3.
[b] The results are expressed as the ratio between the concentrations of McAb required to achieve an identical ELISA response (1.5 Absorbance) when incubated on microtiter plates coated with 0.5 μg/ml D-Lys[8]-Cs-BSA or with Thr[2]Cs-BSA.

TABLE 5

Recognition of Cs-derivatives modified singly at each amino acid residue by 5 monoclonal antibodies belonging to the 5 specificity groups.

| Original | Replacement residue | McAb group | G7 1.1 I | H4 1.3 II | H6 1.5 III | B11 1.4 IV | C4 2.2 V |
|---|---|---|---|---|---|---|---|
| MeBint[1] | 3'desoxy | | 0.6 | 1.2 | 0.0 | 0.4 | <0.0 |
| | 3'-O-acetyl | | 0.1 | 1.1 | 0.6 | 0.7 | 0.2 |
| | ethylmethyl-Me-Thr | | <0.0 | 0.7 | <0.0 | <0.0 | 0.2 |
| | 8'-hydroxy | | 0.0 | <0.0 | <0.0 | <0.0 | 0.0 |
| Abu[2] | aThr | | <0.0 | 1.5 | 1.1 | 0.0 | 0.3 |
| | Ser | | <0.0 | 0.9 | 0.6 | 0.0 | 0.2 |
| | Ala | | 0.2 | ND | 0.0 | 0.4 | 0.1 |
| Sar[3] | D-MeAla | | 1.2 | 1.3 | 1.4 | <0.0 | 1.2 |
| | O-Acetyl-MeSer | | 1.2 | 2.1 | 2.2 | 0.4 | 1.5 |
| MeLeu[4] | MeAla | | <0.0 | 1.8 | 1.2 | 0.3 | 0.1 |
| | MePhe | | <0.0 | 0.7 | 2.3 | 0.2 | 0.0 |
| Val[5] | NVa[2], Nva[5] | | 0.5 | 1.2 | 0.2 | 0.2 | 0.1 |
| | MeLeu | | 1.0 | 1.2 | 0.3 | 0.0 | <0.0 |
| | Met | | <0.0 | 1.5 | <0.0 | 0.0 | <0.0 |
| MeLeu[6] | McAla | | 0.7 | 0.9 | 2.7 | 0.0 | 1.2 |
| | MePhe | | 0.1 | 1.2 | 1.7 | 0.0 | 1.3 |
| Ala[7] | Abu | | <0.0 | 0.0 | 0.0 | 0.0 | <0.0 |
| D-Ala[8] | D-Ser | | 1.3 | 0.0 | <0.0 | 0.1 | 0.3 |
| | D-Thr | | >2.0 | 0.0 | <0.0 | 0.4 | 1.2 |
| | Boc-D-Lys | | 2.0 | 0.6 | 0.0 | 0.3 | 1.2 |
| MeLeu[9] | MeAla | | 1.4 | <0.0 | 0.0 | 1.7 | 1.9 |
| | MePhe | | 0.3 | 0.0 | 0.1 | 1.2 | 1.8 |
| MeAla[10] | MeAla | | <0.0 | 0.4 | 0.0 | 0.1 | 0.8 |
| | MePhe | | <0.0 | 0.5 | 0.2 | 1.6 | 1.3 |
| MeVal[11] | MeIle | | 0.4 | 0.0 | 0.0 | 0.2 | 0.3 |
| | aMeIle | | 0.0 | 0.3 | 0.3 | <0.0 | 0.0 |

Results are expressed as the $log_{10}$ difference in the concentrations of Cs-derivatives and unmodified Cs required to achieve 50% inhibition in ELISA.
Superscript is position of residue in Cs.

EXAMPLE IV

A. Western Blot to Determine binding to gag Protein

A western blot test was performed according to the procedure outlined in Luban, J. and Goff, S. (1991) Binding of Human Immunodeficiency Virus Type 1 (HIV-1) RNA to Recombinant HIV-1 gag Polyprotein. J. Virology 65:3203–3212.

Results are demonstrated in FIG. 9. Lane 1 shows the results of the test using an antibody raised to p24 segment of gag protein. This segment has the active sequence in it. Lanes 2 through 23 show the results of the test using various monoclonal antibodies to cyclosporine A. Lane 9 represents the antibody B-11 1.4 Lane 24 is the control with no antibody.

B. Inhibition of binding of B-11 1.4 to p24 by Cyclophilin A

Blocking antibody binding to p24 by cyclophilin A by preincubating the p24-coated plate with (1 ug/ml in same buffer as other ELISA) with purified human cyclophilin A (a generous gift from Dr. Robert E. Handschumacher, Yale University) at the indicated concentrations in PBS for 1 hr at 37° C. We observed a linear inhibition of antibody binding by cyclophilin A indicating that either cyclophilin competed with the antibody for it's binding site or that cyclophilin binding to p24 sterically blocked the antibody binding site. See FIG. 10.

C. Inhibition of binding of B-11 1.4 by Cyclosporine A

To demonstrate that the B-11 1.4 monoclonal antibody reacts with non-denatured p24 we set up an ELISA.

Ninety-six well plates (Corning 25855) were coated with recombinant p24 produced in a baculovirus expression system (American Biotechnologies, Inc., Cambridge, Mass.) at 1 ug/ml in 0.1 N $NaHCO_3$, pH 9.3, for 2.5 hrs at 37° C. Plates were then blocked with 2% fetal calf serum in phosphate buffered saline with 0.1% Tween-20 for 1 hr at 37° C. B-11 1.4 ascites fluid was preincubated with Cyclosporine A (Sandoz Research Institute) at the indicated concentrations for 1 hr at 37° C., and then incubated with the p24-coated plates for 90 min at 37° C. Bound B-11 1.4 was then detected in a peroxidase reaction as previously described in Cacalano, et al. Molec. Immunol. 2:107–18 (1992). Specificity of B-11 1.4 binding to native p24 was demonstrated by the linear inhibition of binding by cyclosporine A. See FIG. 11.

EXAMPLE V

Clinical uses of the compositions of the subject invention

A. Occupational Exposure to HIV-1

Health care workers exposed to HIV-1-contaminated blood or other bodily fluids can become infected with the virus. Common routes of exposure include, but are in no way limited to, the following: penetration of the skin by an uncapped syringe needle coated with HIV-1-containing bodily fluids ("needle-stick-injury"); cuts caused by scalpels or other instruments during surgery on HIV-1-infected individuals; and splashes of blood or other bodily fluids in the eyes or on cracked skin.

To reduce the risk of HIV-l transmission in the health care setting, the composition of matter or antibody of the subject invention would be administered to a health care worker who was exposed to HIV-1-contaminated fluids, by routes such as those listed above. These may be administered by, inter alia, intravenous bolus, continual IV infusion, intramuscular injection, subcutaneous injection or directly to the wound or exposed skin. A combination of these routes may be used. Depending on the route of administration and the nature of the treatment, the composition of the subject invention might be given continuously or intermittently. The treatment may be most effective if the composition were administered soon after the exposure as possible, for example within one or two hours after exposure.

B. Mother To Infant Transmission of HIV-1

Newborns of HIV-1-infected mothers often become infected with HIV-1. In many cases, infection occurs around the time of birth, due to the exposure to the baby to HIV-1-contaminated blood and other bodily fluids from the mother.

To reduce the risk of HIV-1 transmission in this setting, the composition of matter or antibody of the subject invention would be administered to the other prior to delivery, or to the baby after delivery, or to both. The possible routes of administration include those listed surra. The purpose of treating the mother would be to reduce the infectivity of the maternal blood or other bodily fluids prior to delivery. As an example, the treatment may comprise delivering to the mother a series of intravenous bolus injections of the composition starting several hours or more before birth. Subsequently, the newborn would be treated with the composition in order to reduce the infectivity of any virus which had entered its body around the time of birth. For example, within one or two hours after birth, the newborn may be treated with a continuous IV infusion of the composition for several days.

References

1. Borel, J. F., *Transplant Proc.* 1981; 13: 344.
2. Borel, J. F., *Progr. Allergy* 1986; 38: 474.
3. Beveridge, T., *Transplantation Proceed.* 1983; 15: 433.
4. Shaw, L. M., Bowers, L., Demers, L., Freeman, D., Moyer, T., Sanghvi, A., and Sellman, H., *Clin. Chem.* 1987; 33: 1269.
5. Donatsch, P., Abisch, E., Homberger, M., Traber, R., Trapp, M. and Voges, R., *J. Iminunoassay* 1981; 2: 19.
6. Quesniaux, V. F. J., Tees, R., Schrier, M. H., Wenger, R. M., Donatsch, P. and Van Regenmortel, M. H. V. *Prog. Allergy* 1986; 38: 108.
7. Bayley, H. In: T. S. Work and R. H. Burdon (Eds.), "Laboratory Techniques in Biochemistry and Molecular Biology, Photogenerated Reagents in Biochemistry and Molecular Biology." Elsevier, Amsterdam p. 15. (1983).
8. Wenger, R. M, "Progress in the Chemistry of Organic Natural Products," 50, p. 123 (1986).
9. Erlanger, A., *Methods in Enzymology,* 1980; 70: 85.
10. Hestrin, S., *J. Biol. Chem.* 1949; 180; 249.
11. Cohen, W. and Erlanger, B. F., *Biochem. Biophys. Acta* 1961; 52: 604.
12. Sandoz Ltd. Insert of "Ciclosporin RIA-Kit," Fifth Edition, Basle, Switzerland (1986).
13. Galardy, R. E., Craig, L. C. and Printz, M. P., *Nature* (*London*) *New Biol.* 1973; 242: 127.
14. Wenger, R. M., *Transplant, Proc.* 1986; 18, Suppl. 5: 213.
15. Traber, T., Kuh, M., Rueegger, A., Lichti, H., Loosli, H. R., and von Wartburg, A. *Helvetia Chimica Act* 1977; 59: 1480.
16. Wenger, R., *Transplant Proc.,* 1983; Suppl. 1: 2280.
17. Petcher, T. J., Weber, H. P., and Rueegger, A., *Helvetia ChiMica Acta* 1976; 59: 1480.
18. Kahan, B. D., *Am. J. Disease* 1984; 3: 444.
19. Chowdhry, V., Vaughan, R., and Westheimer, F. H., *Proc. Natl. Acad. Sci. USA* 1976; 73: 1406.
20. Gupta, C. M., Radhakrishnan, R., Gerber, G. E., Osen, W. L. Quay, S. C., and Khorana, H. G., *Proc. Natl. Acad. Sci. USA* 1979; 76: 2595.
21. Pascual, A., Casanova, J., and Samuels, H. H., *J. Biol. Chem.* 1982; 257: 9640.
22. Guesdon, J. L., Ternynck, T., and Avrameas, S., *J. Histochem. Cytochem.* 1979; 27: 1131.
23. Cleveland, WL. L, Wood, I., Cone, R. E., Iverson, G. M., Rosenstein, R. W., Gershon, R. K., and Erlanger, B. F. *Proc. Natl. Acad. Sci. USA* 1981; 78: 7697.
24. Habee, A. F. S., *Anal. Biochem.* 1966; 14: 328.
25. Bethell, G. S., Ayers, J. S., Hancock, W. S., and Hearn, M. T. W., *J. Biol. Chem.* 1979; 254–2572.
26. Cacalano, N. A., Cleveland, W. L., and Erlanger, B. F., (1989). *J. Immun. Meth.,* 118, 257–263.
27. Kearnery, J. F., Radbruch, A., Liesegang, B., and Rajewsky, K., (1979) *J. Immun.,* 123, 1548–1550.
28. Quesniaux, V., Tees, R., Schreier, M. H., Wenger, R. M., and Van Regenmortel, H. V., (1987b) *Molec. Immun.,* 24, 1159–1168.
29. Sharon, J., Morrison, S. L., and Kabat, E. A., (1979) *Proc. natn. Acad. Sci. U.S.A.,* 76, 1420–1424.
30. Luban, J., Bossolt, K. L., Frande, E. K., Kalpana, G. V. and Goff, S. P., (1993) *Cell,* 73, 1067–1078.

What is claimed is:

1. A method of testing whether a composition of matter inhibits binding between an HIV-1 p24 gag protein and a detectably labeled cyclosporine-specific antibody which cross reacts with HIV-1 p24 gag protein which comprises:

a) immobilizing the composition of matter, wherein the composition of matter has the structure:

wherein a plurality of R's are X and the remainder are H, wherein X is a ligand comprising a reactive group and wherein X is bonded to the composition of matter by a photochemical reaction between a hydrogen of cyclosporine A and a photochemically activatable precursor of X;

b) contacting the immobilized composition of matter from (a) with a mixture of HIV-1 p24 gag protein and a detectably labeled antibody which specifically binds to N-methyl leucine residues 9 and 10 of cyclosporine and cross reacts with HIV-1 p24 gag protein under conditions allowing for the labelled antibody to bind to the immobilized composition of matter from (a) and form a complex therewith;

c) separating any unbound labeled antibody from any complex formed in (b);

d) detecting any labeled antibody bound to the complex in (b); and e) quantitating the amount of labeled antibody from (d), a decrease in the amount of antibody bound to the composition of matter after incubation with the HIV-1 p24 gag protein in step (b) compared to the amount of antibody bound to the composition of matter in the absence of HIV-1 p24 gag protein indicating that the composition of matter inhibits binding between the HIV-1 p24 gag protein and the detectably labeled antibody.

2. The method of claim 1 wherein the detectably labeled antibody which specifically binds to N-methyl leucine residues 9 and 10 of cyclosporine is the monoclonal antibody B-11 1.4 produced by the hybridoma cell line having ATCC Accession No. HB-11853.

3. The method of claim 2 wherein the detectably labeled antibody is labeled with an enzyme, dye, fluorescent marker, colored bead, radioactive isotope or biotin.

4. A kit for testing whether a composition of matter inhibits binding between HIV-1 p24 gag protein and a detectably labeled cyclosporine-specific antibody which cross reacts with HIV-1 p24 gag protein which comprises:

a) a plate comprising a plurality of wells;

b) the composition of matter immobilized upon the wells, wherein the composition of matter has the structure:

-continued wherein a plurality of R's are X and the remainder are H, wherein X is a ligand comprising a reactive group and wherein X is bonded to the composition of matter by a photochemical reaction between a hydrogen of cyclosporine A and a photochemically activatable precursor of X; and c) a solution comprising the detectably labeled cyclosporine-specific antibody which cross reacts with HIV-1 p24 gag protein and which specifically binds to N-methyl leucine residues 9 and 10 of cyclosporine; and d) a solution comprising the HIV-1 p24 gag protein.

5. The kit of claim 4 wherein the detectably labeled antibody which specifically binds to N-methyl leucine residues 9 and 10 of cyclosporine is the monoclonal antibody B-11 1.4 produced by the hybridoma cell line having ATCC Accession No. HB-11853.

6. The kit of claim 4 wherein the detectably labeled antibody is labeled with an enzyme, dye, fluorescent marker, colored bead, radioactive isotope or biotin.

* * * * *